United States Patent
Horseman

(10) Patent No.: US 8,872,640 B2
(45) Date of Patent: Oct. 28, 2014

(54) SYSTEMS, COMPUTER MEDIUM AND COMPUTER-IMPLEMENTED METHODS FOR MONITORING HEALTH AND ERGONOMIC STATUS OF DRIVERS OF VEHICLES

(75) Inventor: Samantha J. Horseman, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 308 days.

(21) Appl. No.: 13/540,374

(22) Filed: Jul. 2, 2012

(65) Prior Publication Data

US 2013/0009761 A1    Jan. 10, 2013

Related U.S. Application Data

(60) Provisional application No. 61/504,638, filed on Jul. 5, 2011, provisional application No. 61/659,831, filed on Jun. 14, 2012, provisional application No. 61/659,790, filed on Jun. 14, 2012, provisional application No. 61/659,796, filed on Jun. 14, 2012, provisional application No. 61/659,800, filed on Jun. 14, 2012, provisional application No. 61/659,807, filed on Jun. 14, 2012, provisional application No. 61/659,810, filed on Jun. 14, 2012, provisional application No. 61/659,818, filed on Jun. 14, 2012, provisional application No. 61/659,824, filed on Jun. 14, 2012, provisional application No. 61/664,387, filed on Jun. 26, 2012, provisional application No. 61/664,399, filed on Jun. 26, 2012, provisional application No. 61/664,414, filed on Jun. 26, 2012.

(51) Int. Cl.
| | | |
|---|---|---|
| B60Q 1/00 | (2006.01) | |
| G08B 23/00 | (2006.01) | |
| B60K 28/06 | (2006.01) | |
| A61B 5/11 | (2006.01) | |
| A61B 5/18 | (2006.01) | |
| A61B 5/0476 | (2006.01) | |
| A61B 5/00 | (2006.01) | |
| B60W 40/08 | (2012.01) | |
| A61B 5/0402 | (2006.01) | |
| A61B 5/0205 | (2006.01) | |

(52) U.S. Cl.
CPC .............. *A61B 5/18* (2013.01); *A61B 5/6803* (2013.01); *B60W 2040/0818* (2013.01); *B60K 28/06* (2013.01); *A61B 5/0402* (2013.01); *A61B 5/486* (2013.01); *B60W 40/08* (2013.01); *B60W 2040/0872* (2013.01); *A61B 5/6893* (2013.01); *A61B 5/0205* (2013.01); *A61B 5/1114* (2013.01); *A61B 2562/046* (2013.01); *B60W 2540/22* (2013.01); *A61B 2503/40* (2013.01); *A61B 5/0476* (2013.01)
USPC ....................................... 340/425.5; 340/576

(58) Field of Classification Search
CPC ................. B60W 2540/22; B60W 2040/0818; B60W 2040/0872; B60W 40/08; A61B 5/18; A61B 5/1114; A61B 5/486; A61B 5/6893; B60K 28/06; B60N 2002/0268; B60R 2021/01566; B60R 21/015
USPC ........ 180/271; 340/425.5, 573.1, 576; 701/34
See application file for complete search history.

(56) References Cited

U.S. PATENT DOCUMENTS

| 5,304,112 A | 4/1994 | Mrklas et al. |
| 5,792,047 A | 8/1998 | Coggins |

(Continued)

FOREIGN PATENT DOCUMENTS

| AU | 767533 | 11/2003 |
| EP | 1407713 | 9/2008 |

(Continued)

OTHER PUBLICATIONS

"Making a Difference", World Health Organisation, Geneva: WHO, 1999, pp. 1-136.

(Continued)

*Primary Examiner* — Brian Zimmerman
*Assistant Examiner* — Thomas McCormack
(74) *Attorney, Agent, or Firm* — Bracewell & Giuliani LLP; Jeffrey S. Whittle; Brad Y. Chin

(57) ABSTRACT

Provided are embodiments of systems, computer medium and computer-implemented methods for monitoring a status of a driver when driving a vehicle. A system including a set of sensors configured to be disposed in the vehicle to collect driver status data. The system processing the driver status data to determine whether the driver is experiencing a health condition or crisis, and whether the driver's body position is ergonomic. In response to a health condition, generating a health alert indicative of the health condition. In response to the driver a health crisis generating a health alert indicative of the health crisis and inhibiting operation of the vehicle. In response to the driver's body position not being ergonomic, identifying and providing adjustments in the body position of the driver that need to be made for the driver to be positioned in a an ergonomically acceptable body position.

8 Claims, 12 Drawing Sheets

(56) References Cited

U.S. PATENT DOCUMENTS

| | | | |
|---|---|---|---|
| 6,104,296 | A | 8/2000 | Yasushi et al. |
| 6,190,314 | B1 | 2/2001 | Ark et al. |
| 6,281,594 | B1 | 8/2001 | Sarich |
| 6,291,900 | B1 | 9/2001 | Tiemann et al. |
| 6,293,771 | B1 | 9/2001 | Haney et al. |
| 6,309,342 | B1 | 10/2001 | Blazey et al. |
| 6,381,577 | B1 | 4/2002 | Brown |
| 6,452,862 | B1 | 9/2002 | Tomotani |
| 6,572,558 | B2 | 6/2003 | Masakov et al. |
| 6,585,645 | B2 | 7/2003 | Hutchinson |
| 6,673,027 | B2 | 1/2004 | Fischer |
| 6,768,246 | B2 | 7/2004 | Pelrine et al. |
| 6,828,908 | B2 | 12/2004 | Clark |
| 6,832,987 | B2 | 12/2004 | David et al. |
| 6,982,497 | B2 | 1/2006 | Rome |
| 7,005,757 | B2 | 2/2006 | Pandian |
| 7,027,621 | B1 | 4/2006 | Prokoski |
| 7,109,872 | B2 | 9/2006 | Balaban et al. |
| 7,188,151 | B2 | 3/2007 | Kumar et al. |
| 7,233,312 | B2 | 6/2007 | Stern et al. |
| 7,315,249 | B2 | 1/2008 | Littell |
| 7,407,484 | B2 | 8/2008 | Korman |
| 7,624,037 | B2 | 11/2009 | Bost |
| 7,652,582 | B2 | 1/2010 | Littell et al. |
| 7,771,318 | B2 | 8/2010 | Narayanaswami |
| 7,849,115 | B2 | 12/2010 | Reiner |
| 7,958,002 | B2 | 6/2011 | Bost |
| 7,972,266 | B2 | 7/2011 | Gobeyn et al. |
| 8,015,022 | B2 | 9/2011 | Gore |
| 8,030,786 | B2 | 10/2011 | Jackson et al. |
| 8,487,456 | B2 | 7/2013 | Donelan et al. |
| 2001/0041845 | A1 | 11/2001 | Kim |
| 2003/0058111 | A1 | 3/2003 | Lee et al. |
| 2003/0154107 | A1 | 8/2003 | Medvedeff |
| 2003/0209113 | A1 | 11/2003 | Brooks et al. |
| 2003/0226695 | A1 | 12/2003 | Mault |
| 2005/0075542 | A1 | 4/2005 | Goldreich |
| 2005/0101845 | A1 | 5/2005 | Nihtila |
| 2006/0135857 | A1 | 6/2006 | Ho et al. |
| 2006/0183980 | A1 | 8/2006 | Yang |
| 2006/0267747 | A1 | 11/2006 | Kondo |
| 2007/0017531 | A1 | 1/2007 | Large |
| 2007/0038153 | A1 | 2/2007 | Basson et al. |
| 2007/0139362 | A1 | 6/2007 | Colton et al. |
| 2007/0191727 | A1 | 8/2007 | Fadem |
| 2008/0015422 | A1 | 1/2008 | Wessel |
| 2008/0052837 | A1 | 3/2008 | Blumberg |
| 2008/0146892 | A1 | 6/2008 | LeBoeuf et al. |
| 2008/0171914 | A1 | 7/2008 | Ouwerkerk et al. |
| 2008/0177158 | A1 | 7/2008 | Teller et al. |
| 2008/0177614 | A1 | 7/2008 | An et al. |
| 2008/0218331 | A1 | 9/2008 | Baillot |
| 2008/0242521 | A1 | 10/2008 | Einav |
| 2008/0306357 | A1 | 12/2008 | Korman |
| 2008/0306762 | A1 | 12/2008 | James |
| 2009/0002178 | A1 | 1/2009 | Guday et al. |
| 2009/0030767 | A1 | 1/2009 | Morris et al. |
| 2009/0047645 | A1 | 2/2009 | Dibenedetto et al. |
| 2009/0055204 | A1 | 2/2009 | Pennington et al. |
| 2009/0058661 | A1 | 3/2009 | Gleckler et al. |
| 2009/0209829 | A1 | 8/2009 | Yanagidaira |
| 2009/0319297 | A1 | 12/2009 | Hernandez et al. |
| 2010/0014711 | A1 | 1/2010 | Camhi et al. |
| 2010/0049004 | A1 | 2/2010 | Edman |
| 2010/0049541 | A1 | 2/2010 | Pollard et al. |
| 2010/0169219 | A1 | 7/2010 | Sellers et al. |
| 2010/0259043 | A1 | 10/2010 | Balsamo |
| 2010/0283265 | A1 | 11/2010 | Rastegar et al. |
| 2011/0033830 | A1 | 2/2011 | Cherian |
| 2011/0035231 | A1 | 2/2011 | Firminger et al. |
| 2011/0080290 | A1 | 4/2011 | Baxi et al. |
| 2011/0098056 | A1 | 4/2011 | Rhoads et al. |
| 2011/0137669 | A1 | 6/2011 | Bennett |
| 2011/0172744 | A1 | 7/2011 | Davis et al. |
| 2011/0196212 | A1 | 8/2011 | Peters et al. |
| 2011/0213664 | A1 | 9/2011 | Osterhout et al. |
| 2011/0285146 | A1 | 11/2011 | Kozinsky et al. |
| 2012/0007367 | A1 | 1/2012 | Chang |
| 2012/0052971 | A1 | 3/2012 | Bentley |
| 2012/0139731 | A1 | 6/2012 | Razoumov et al. |
| 2012/0154277 | A1 | 6/2012 | Bar-Zeev et al. |
| 2012/0215076 | A1 | 8/2012 | Yang et al. |
| 2012/0271121 | A1 | 10/2012 | Della Torre et al. |
| 2013/0009761 | A1 | 1/2013 | Horseman |
| 2013/0009993 | A1 | 1/2013 | Horseman |
| 2013/0011819 | A1 | 1/2013 | Horseman |
| 2013/0012786 | A1 | 1/2013 | Horseman |
| 2013/0012787 | A1 | 1/2013 | Horseman |
| 2013/0012788 | A1 | 1/2013 | Horseman |
| 2013/0012789 | A1 | 1/2013 | Horseman |
| 2013/0012790 | A1 | 1/2013 | Horseman |
| 2013/0012802 | A1 | 1/2013 | Horseman |
| 2013/0013327 | A1 | 1/2013 | Horseman |
| 2013/0013331 | A1 | 1/2013 | Horseman |
| 2013/0056981 | A1 | 3/2013 | Mullins et al. |

FOREIGN PATENT DOCUMENTS

| | | |
|---|---|---|
| EP | 2151355 | 2/2010 |
| EP | 2248461 A2 | 11/2010 |
| WO | 0128416 | 4/2001 |
| WO | 0186403 | 11/2001 |
| WO | 2005064447 | 7/2005 |
| WO | 2006022465 A1 | 3/2006 |
| WO | 2007016056 A2 | 2/2007 |
| WO | 2007130591 A2 | 11/2007 |
| WO | 2010048145 | 4/2010 |
| WO | 2011020299 | 2/2011 |

OTHER PUBLICATIONS

"National health expenditure data", Centers for Medicare & Medicaid Services, available at: <http://www.cms.gov/Research-Statistics-Data-and-Systems/Statistics-Trends-and-Reports>, accessed Nov. 18, 2013, pp. 1-2.

"Piezo Electric Energy Harvester", Midé Technology Corporation, retrieved Nov. 18, 2013. pp. 1-2.

"Signal Conditioning Piezoelectric Sensors", (PDF) Texas Instruments, Application Report SLOA033A, Sep. 2000, pp. 1-6.

The constitution of the World Health Organization, World Health Organization, WHO Chronicle, 1947, pp. 1-202.

Aldana, S., "Financial Impact of health promotion programs: a comprehensive review of the literature", American Journal of Health Promotion,155, 2001, pp. 296-320.

Aldana, S., Merrill, R., Price, K., Hardy, A., and Hager, R., "Financial impact of a comprehensive multi-site worksite health promotion program", Preventive Medicine, 40, Jul. 2004, pp. 131-137.

Alfredo Vázquez Carazo, "Novel Piezoelectric Transducers for High Voltage Measurements", Jan. 2000 , pp. 1-277.

Baiker, K., Cutler, D., Song, Z., "Worksite wellness programs can generate savings", Health Affairs 29(2), Jan. 2010, pp. 1-8.

Berry, L.L., Mirabito, A.M., Baun, W.B., "What's the Hard Return on Employee Wellness Programs?", Harvard Business Review, Dec. 2010, pp. 1-10.

Chapman, L., "Expert opinions on 'best practice' in worksite health promotion (WHP)", Jul./Aug. 2004, pp. 1-13.

Chapman, L.. "Meta-evaluation of worksite health promotion economic return studies: 2012 Update", Mar./Apr. 2012, pp. 1-13.

Edington, D. W., "Emerging research: a view from one research centre", American Journal of Health Promotion, 15(5), May/Jun. 2001, pp. 341-349.

Edington, M., Karjalainen, T., Hirschland, D., Edington, D.W., "The UAW-GM Health Promotion Program: Successful Outcomes", American Association of Occupational Health Nursing Journal.50, Jan. 2002, pp. 26-31.

Hemp, P., "Presenteeism: At Work—But Out of It", Harvard Business Review, Oct. 2004, pp. 49-58.

Horseman, S. J ., "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.

(56) References Cited

OTHER PUBLICATIONS

Horseman, S.J., "ErgoWELL : An Integrative Strategy", SPE Paper #: SPE-152629. Society of Petroleum Engineers, MEHSSE. Paper and Workshop, Abu Dhabi, 2012, pp. 1-17.
Johns, G., "Presenteeism in the Workplace: A review and research agenda", Journal of Organizational Behavior, Jul. 31, 2009, pp. 519-542.
Priya, S., "Advances in Energy Harvesting Using Low Profile Piezoelectric Transducers", Materials Science & Engineering, Springer, Mar. 2007, pp. 165-182.
Reidel, J.E., Baase, C., "The effect of disease prevention & health promotion on worksite productivity: a literature review", American Journal of Health Promotion, 15:3, Jan./Feb. 2001, pp. 167-191, 243.
Roberts, R.O.,Bergstralh, E.J., Schmidt, L, Jacobsoen,S.J., "Comparison of Self Reported and Medical Record Health Care Utilization Measures", Journal of Clinical Epidemiology, 49:9, Feb. 1996, pp. 989-995.
Copending U.S. Appl. No. 14/102,619 titled "Systems, Computer Medium and Computer-Implemented Methods for Harvesting Human Energy in the Workplace", filed Dec. 11, 2013.
Copending U.S. Appl. No. 14/180,529 titled "Chair Pad System and Associated, Computer Medium and Computer-Implemented Methods for Monitoring and Improving Health and Productivity of Employees" filed Feb. 14, 2014.
Copending U.S. Appl. No. 14/180,533 titled "Chair Pad System and Associated, Computer Medium and Computer-Implemented Methods for Monitoring and Improving Health and Productivity of Employees" filed Feb. 14, 2014.
Copending U.S. Appl. No. 14/180,536 titled "Floor Mat System and Associated, Computer Medium and Computer-Implemented Methods for Monitoring and Improving Health and Productivity of Employees" filed Feb. 14, 2014.
Copending U.S. Appl. No. 14/180,471 titled "Floor Mat System and Associated, Computer Medium and Computer-Implemented Methods for Monitoring and Improving Health and Productivity of Employees" filed Feb. 14, 2014.
Copending U.S. Appl. No. 14/180,993 titled "Systems, Computer Medium and Computer-Implemented Methods for Monitoring and Improving Biometric Health of Employees" filed Feb. 14, 2014.
Copending U.S. Appl. No. 14/181,006 titled "Systems, Computer Medium and Computer-Implemented Methods for Monitoring and Improving Biomechanical Health of Employees" filed Feb. 14, 2014.
Copending U.S. Appl. No. 14/180,978 titled "Systems, Computer Medium and Computer-Implemented Methods for Monitoring and Improving Health and Productivity of Employees" filed Feb. 14, 2014.
International Preliminary Report on Patentability for International Application No. PCT/US2012/045395, dated Jan. 7, 2014. (pp. 1-12).
International Preliminary Report on Patentability for International Application No. PCT/US2012/045401, dated Jan. 7, 2014. (pp. 1-9).
International Preliminary Report on Patentability for International Application No. PCT/US2012/1045407, dated Jan. 7, 2014. (pp. 1-8).
International Preliminary Report on Patentability for International Application No. PCT/US20121/045410, dated Jan. 7, 2014. (pp. 1-8).
International Preliminary Report on Patentability for International Application No. PCT/US2012/045414, dated Jan. 7, 2014. (pp. 1-8).
International Preliminary Report on Patentability for International Application No. PCT/US2012/045419, dated Jan. 7, 2014. (pp. 1-11).
International Preliminary Report on Patentability for International Application No. PCT/US2012/045427, dated Jan. 7, 2014. (pp. 1-10).
International Preliminary Report on Patentability for International Application No. PCT/US2012/045435, dated Jan. 7, 2014. (pp. 1-10).
International Preliminary Report on Patentability for International Application No. PCT/US2012/045452, dated Jan. 7, 2014. (pp. 1-9).
International Preliminary Report on Patentability for International Application No. PCT/US2012/045447, dated Jan. 7, 2014. (pp. 1-8).
International Preliminary Report on Patentability for International Application No. PCT/US2012/045442, dated Jan. 7, 2014. (pp. 1-10).
Centers for Disease Control and Prevention, 2011, "Chronic diseases and health promotion", [online] Availableat: http://www.cdc.gov/chronicdisease/ overview, [Accessed Feb. 2, 2011].
"Research programs—Philips Research", retrieved from <http://www.research.philips.com/programs/index.html>, May 7, 2012. (pp. 1-2).
"Speedy Assessment | Chiropractic Assessment and Patient Education", retrieved from <http://speedyassessment.com/>, May 7, 2012. (pp. 1-3).
"Stress Thermometer", retrieved from <http://www.biof.com/onlinestore/stressthermometer.asp?redirect=yes>, May 7, 2012. (pp. 1-4).
"Biofeedback—MayoClinic.com", retrieved from <http://www.mayoclinic.com/health/biofeedback/MY01072>, May 7, 2012. (pp. 1-2).
Abstract for "Psychosocial job factors and symptoms from the locomotor system—a multicausal analysis", retrieved from <http://www.ncbi.nlm.nih.gov/pubmed/1962160>, May 7, 2012. (p. 1).
Abstract for "Signal Characteristics of EMG at Different Levels of Muscle Tension", retrieved from <http://onlinelibrary.wiley.com/doi/10.1111/.1748-1716.1976.tb10195.x/abstract>, May 7, 2012. (p. 1).
Index for "Micro-NanoMechatronics and Human Science (MHS), 2010 International Symposium Nov. 2010", retrieved from <http://ieeexplore.ieee.org/xpl/mostRecentIssue.jsp?punumber=5658189> Ma 7, 2012. (pp. 1-5).
"Wireless measurement devices—Philips", retreved from <http://www.healthcare.philips.com/us_en/products/telehealth/Products/devices.wpd>, May 7, 2012. (pp. 1-2).
"Philips Research Technology Backgrounder—MyHeart project", retrieved from <http://www.research.philips.com/technologies/heartcycle/myheart-gen.html>, May 7, 2012. (pp. 1-3).
"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).
"Philips Research—Download Pictures", retrieved from <http://www.research.philips.com/downloads/pictures/healthcare-personal.html>, May 7, 2012. (pp. 1-2).
"RJL Systems, Products", retrieved from <http://www.rjlsystems.com/products.shtml>, May 7, 2012. (p. 1).
"MomToBe: The Pregnancy Assistant 3.0", retreved from <http://3d2f.com/programs/4-230-momtobe-the-pregnancy-assistant-download.shtml>, Jun. 11, 2012. (pp. 1-2).
"Clever toilet checks on your health", retrieved from <http://articles.cnn.com/2005-06-28/tech/spark.toilet_1_toilet-toto-bathroom?_s= PM:TECH>, Jun. 28, 2005. (pp. 1-2).
"WorkPace : RSI Injury Prevention Software, Stretch Break Exercise Reminder Software", retrieved from <http://www.workpace.com/>, Sep. 14, 2012. (p. 1).
"Workrave", retrieved from <http://www.workrave.org/>, Sep. 14, 2012. (p. 1).
"Office Athlete Software Prevents Common Repetitive Stress Injuries", retrieved from <http://www.officeathlete.com/>, Sep. 14, 2012. (pp. 1-2).
"Cardinus Risk Management | Ergonomic & DSE Risk Assessments", retrieved from <http://www.cardinus.com/>, Sep. 12, 2012. (pp. 1-2).
"Kinect—Xbox.com", retrieved from <http://www.xbox.com/en-US/kinect>, Jun. 11, 2012. (pp. 1-3).
"Augmented Reality", retrieved from <http://en.wikipedia.org/wiki/Augmented_reality>, May 30, 2012. pp. 1-18.
"Electroencephalography (EEG)", retieved from <http://www.emedicinehealth.com/script/main/art.asp?articlekey-59319&pf=3&page=1>, Jun. 11, 2012. (pp. 1-4).
"Emotiv|EEG System|Electroencephalography", retrieved from <www.emotiv.com/index.asp>, Jun. 11, 2012. (pp. 1-2).

(56) References Cited

OTHER PUBLICATIONS

"EmotivEPOC Software Devlopment Kit", retrieved from <www.emotiv.com/store/hardware/epoc-bci-eeg/developer-neuroheadset/>, Jun. 11, 2012. (pp. 1-2).
Chapman, Larry S. MPH, "Meta-evaluation of Worksite Health Promotion Economic Return Studies: 2005 Update", Jul./Aug. 2005. (pp. 1-11).
"OSHA Ergonomic Solutions: Computer Workstations eTool—Checklists", retrieved from <www.osha.gov/SLTC/etools/computerworkstations/checklist.html>, Jun. 11, 2012. (pp. 1-5).
"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).
"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).
"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).
"OSHA Ergonomic Solutions: Computer Workstations eTool—Workstations eTool", retrieved from <www.osha.gov/SLTC/etools/computerworkstations/index.html>, Jun. 11, 2012. (p. 1).
"The Wellness Imperative, Creating More Effective Organizations", World Economic Forum, 2010. (pp. 1-20).
Berry, Leonard et al., "What's the Hard Return on Employee Wellness Programs?", Harvard Business Review, Dec. 2010. (pp. 1-10).
"Pulse Oximetry" SparkFun Electronics, Oct. 7, 2005. (p. 1).
International Search Report & Written Opinion for International Application No. PCT/US2012/045447, dated Jan. 18, 2013. (pp. 1-12).
International Search Report & Written Opinion for International Application No. PCT/US2012/045407, dated Jan. 23, 2013. (pp. 1-15).
International Search Report & Written Opinion for International Application No. PCT/US2012/045401, dated Feb. 5, 2013. (pp. 1-13).
International Search Report & Written Opinion for International Application No. PCT/US2012/045435, dated Jan. 25, 2013. (pp. 1-14).
International Search Report & Written Opinion for International Application No. PCT/US2012/045410, dated Jan. 31, 2013. (pp. 1-13).
International Search Report & Written Opinion for International Application No. PCT/US2012/045414, dated Mar. 25, 2013. (pp. 1-13).
Copending U.S. Appl. No. 13/540,028 titled "Systems, Computer Medium and Computer-Implemented Methods for Monitoring and Improving Cognitive and Emotive Health of Employees", filed Jul. 2, 2012.
Copending U.S. Appl. No. 13/540,067 titled "Computer Mouse System and Associated, Computer Medium and Computer-Implemented Methods for Monitoring and Improving Health and Productivity of Employees", filed Jul. 2, 2012.
Copending U.S. Appl. No. 13/540,095 titled "Chair Pad System and Associated, Computer Medium and Computer-Implemented Methods for Monitoring and Improving Health and Productivity of Employees", filed Jul. 2, 2012.
Copending U.S. Appl. No. 13/540,124 titled "Floor Mat System and Associated, Computer Medium and Computer-Implemented Methods for Monitoring and Improving Health and Productivity of Employees", filed Jul. 2, 2012.
Copending U.S. Appl. No. 13/540,153 titled "Systems, Computer Medium and Computer-Implemented Methods for Monitoring and Improving Biometric Health of Employees", filed Jul. 2, 2012.
Copending U.S. Appl. No. 13/540,180 titled "Systems, Computer Medium and Computer-Implemented Methods for Monitoring and Improving Biomechanical Health of Employees", filed Jul. 2, 2012.
Copending U.S. Appl. No. 13/540,208 titled "Systems, Computer Medium and Computer-Implemented Methods for Coaching Employees Based Upon Monitored Health Conditions Using an Avatar", filed Jul. 2, 2012.
Copending U.S. Appl. No. 13/540,300 titled "Systems, Computer Medium and Computer-Implemented Methods for Monitoring Health of Employees Using Mobile Devices", filed Jul. 2, 2012.
Copending U.S. Appl. No. 13/540,335 titled "Systems, Computer Medium and Computer-Implemented Methods for Providing Health Information to Employees Via Augmented Reality Display", filed Jul. 2, 2012.
Copending U.S. Appl. No. 13/540,262 titled "Systems, Computer Medium and Computer-Implemented Methods for Monitoring and Improving Health and Productivity of Employees", filed Jul. 2, 2012.
"Footrests—Adjustable Footrest Solutions for the Office", Ergo in Demand, Aug. 20, 2009, pp. 1-4, Ergo in Demand Inc., www.ergoindemand.com/footrest.html.
Berger et al., "Investing in Healthy Human Capital", Journal of Occupational Environmental Medicine vol. 45, No. 12, dated Dec. 2003; pp. 1213-1225.
Brown et al., "Prowess Proactive Wellness Environment Support System", Dec. 10, 2009, pp. 1-19, www.hsi.gatech.edu/onsitecenter/index.php/PROWESS.
Campbell et al., "The Rise of People-Centric Sensing", IEEE Computer Society, 2008, pp. 12-21, IEEE.
Georgia Tech, "Prowess Proactive Wellness Environment Support System", Dec. 12, 2009, pp. 1-27, www.hsi.gatech.edu/onsitecenter/index.php/PROWESS.
Goetzel et al., "Estimating the Return-on-Investment From Changes in Employee Health Risks on the Dow Chemical Company's Health Care Costs", Journal of Occupational Environmental Medicine vol. 47, No. 8, dated Aug. 2005; pp. 759-768.
Goetzel et al., "Health, Absence, Disability, and Presenteeism Cost Estimates of Certain Physical and Mental Health Conditions Affecting U.S. Employers", Journal of Occupational Environmental Medicine vol. 46, No. 4, dated Apr. 2004; pp. 398-412.
Goetzel et al., "Second-Year Results of an Obesity Prevention Program at the Dow Chemical Company", Journal of Occupational Environmental Medicine vol. 52, No. 3, dated Mar. 2010; pp. 291-302.
Goetzel et al., "The Health and Productivity Cost Burden of the "Top 10" Physical and Mental Health Conditions Affecting Six Large U.S. Employers in 1999", Journal of Occupational Environmental Medicine vol. 45, No. 1, dated Jan. 2003; pp. 5-14.
Goetzel et al., "The Long-Term Impact of Johnson & Johnson's Health & Wellness Program on Employee Health Risks", Journal of Occupational Environmental Medicine vol. 44, No. 5, dated May 2002; pp. 417-424.
Goetzel et al., "The Relationship Between Modifiable Health Risks and Health Care Expenditures: An Analysis of the Multi-Employer HERO Health Risk and Cost Database", Journal of Occupational Environmental Medicine, vol. 40, No. 10; pp. 1-30.
Goetzel et al., "The Workforce Wellness Index", Journal of Occupational Environmental Medicine vol. 55, No. 3, dated Mar. 2013; pp. 272-279.
Goetzel et al., "The Predictive Validity of the HERO Scorecard in Determining Future Health Care Cost and Risk Trends", Journal of Occupational Environmental Medicine vol. 56, No. 2, dated Feb. 2014; pp. 136-144.
Kelly et al., "The Novartis Health Index: A Method for Valuing the Economic Impact of Risk Reduction in a Workforce" Journal of Occupational Environmental Medicine vol. 52, No. 5, dated May 2010; pp. 528-535.
Prochaska et al., "The Well-Being Assessment for Productivity", Journal of Occupational Environmental Medicine vol. 53, No. 7, dated Jul. 2011; pp. 735-768.
Slater et al., "Taking Steps: The Influence of a Walking Technique on Presence in Virtual Reality", ACM Transactions on Computer-Human Interaction, Sep. 1995, pp. 201-219, vol. 2 No. 3.
Sullivan, "Making the Business Case for Health and Productivity Management", Journal of Occupational Environmental Medicine vol. 46, No. 6 suppl, dated Jun. 2004; pp. S56-S61.

(56) References Cited

OTHER PUBLICATIONS

World Economic Forum, "The Workplace Wellness Alliance-Making the Right Investment: Employee Health and the Power of Metrics" dated Jan. 2013; pp. 1-36.
USPTO Communication for U.S. Appl. No. 13/540,262, mailed Apr. 9, 2014. (pp. 1-56).
USPTO Communication for U.S. Appl. No. 13/540,153, mailed Apr. 9, 2014. (pp. 1-50).
USPTO Communication for U.S. Appl. No. 13/540,180, mailed Apr. 9, 2014. (pp. 1-49).
USPTO Communication for U.S. Appl. No. 13/540,335, mailed Apr. 25, 2014. (pp. 1-48).
International Search Report and Written Opinion for International Application No. PCT/US2012/045427, dated Dec. 3, 2012, pp. 1-14.
International Search Report and Written Opinion for International Application No. PCT/US2012/045419, dated Dec. 6, 2012, pp. 1-16.
International Search Report and Written Opinion for International Application No. PCT/US2012/045395, dated Dec. 3, 2012, pp. 1-16.
International Search Report and Written Opinion for International Application No. PCT/US2004/045442, dated Nov. 7, 2012, pp. 1-14.
International Search Report and Written Opinion for International Application No. PCT/US2012/045452, dated Dec. 3, 2012, pp. 1-14.
"www.mydailyhealth.com" retrieved from the "wayback machine" (pp. 1-20).
Health/Medical Writers eHealthcareWorld 2000. (May 1). MyDailyHealth.com (pp. 1-3).
Murray Hill, Well Med Team to Offer Next Generation Online Preventive Health Services. (Nov. 3). PR Newswire, 1. (pp. 1-3).
Copending U.S. Appl. No. 14/035,670 titled "Computer Mouse for Monitoring and Improving Health and Productivity of Employees", filed Sep. 24, 2013.
Copending U.S. Appl. No. 14/035,717 titled "Computer Mouse System and Associated Computer Medium for Monitoring and Improving Health and Productivity of Employees", filed Sep. 24, 2013.
Copending U.S. Appl. No. 14/035,732 titled "Methods for Monitoring and Improving Health and Productivity of Employees Using a Computer Mouse System", filed Sep. 24, 2013.
Copending U.S. Appl. No. 14/043,898 titled "Systems, Computer Medium and Computer-Implemented Methods for Quantifying and Employing Impacts of Workplace Wellness Programs", filed Oct. 2, 2013.
USPTO Communicaiton for U.S. Appl. No. 13/540,067 mailed Oct. 17, 2013. (pp. 1-39).

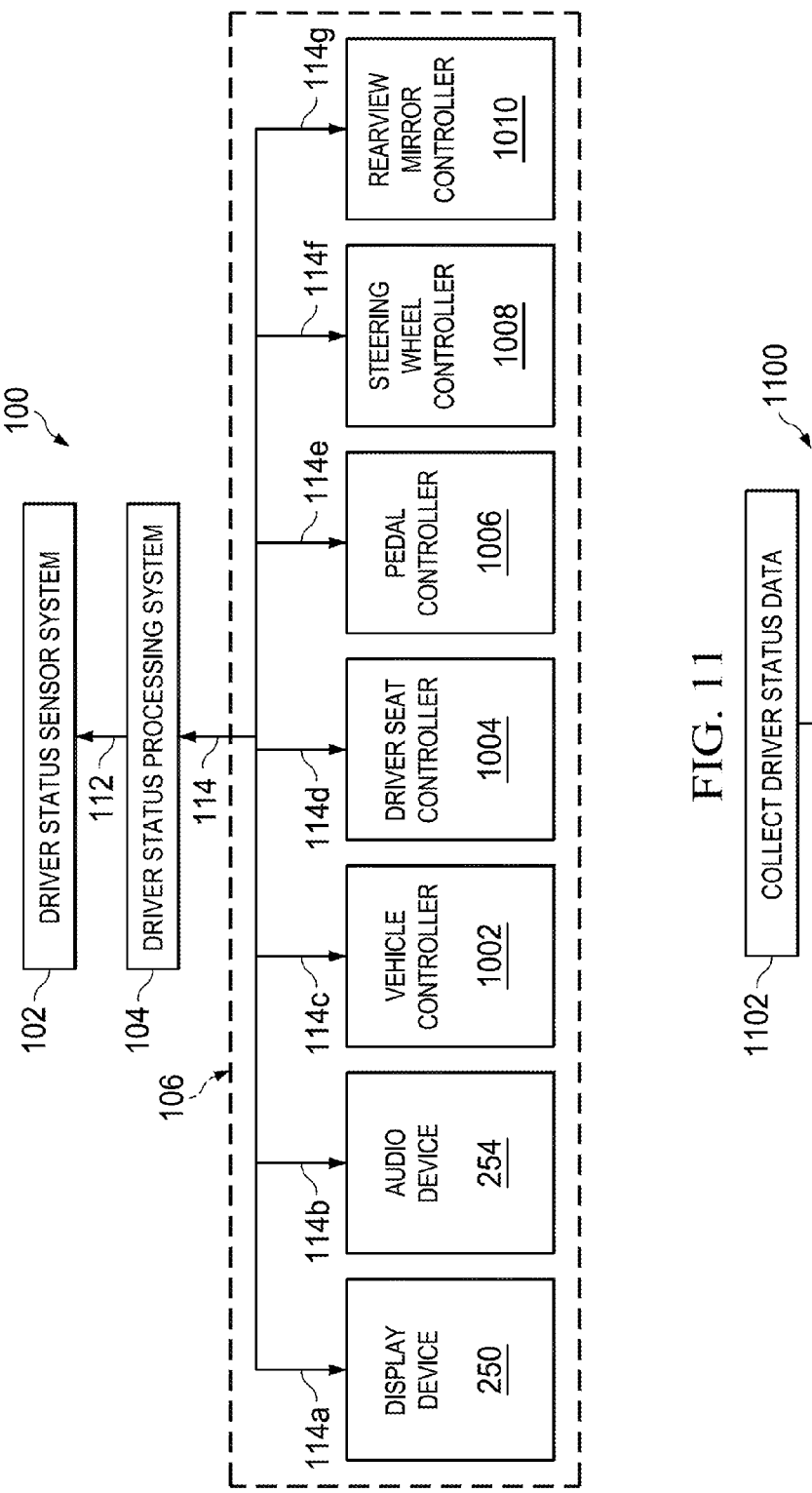

US 8,872,640 B2

SYSTEMS, COMPUTER MEDIUM AND COMPUTER-IMPLEMENTED METHODS FOR MONITORING HEALTH AND ERGONOMIC STATUS OF DRIVERS OF VEHICLES

RELATED APPLICATIONS

This application claims the benefit of U.S. Provisional Patent Application No. 61/664,414, filed on Jun. 26, 2012, and titled "SYSTEMS, COMPUTER MEDIUM AND COMPUTER-IMPLEMENTED METHODS FOR MONITORING HEALTH AND ERGONOMIC STATUS OF DRIVERS OF VEHICLES", U.S. Provisional Patent Application No. 61/504,638, filed on Jul. 5, 2011, and titled "SYSTEM, COMPUTER PROGRAM PRODUCT AND COMPUTER-IMPLEMENTED METHOD FOR IMPROVING AND MONITORING THE HEALTH AND PRODUCTIVITY OF EMPLOYEES", U.S. Provisional Patent Application No. 61/659,831, filed on Jun. 14, 2012, and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,790, filed on Jun. 14, 2012, and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. Provisional Patent Application No. 61/659,796, filed on Jun. 14, 2012, and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,800, filed on Jun. 14, 2012, and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,807, filed on Jun. 14, 2012, and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,810, filed on Jun. 14, 2012, and titled "SYSTEMS, COMPUTER MEDIUM AND COMPUTER-IMPLEMENTED METHODS FOR MONITORING AND IMPROVING BIOMETRIC HEALTH OF EMPLOYEES", U.S. Provisional Patent Application No. 61/659,818, filed on Jun. 14, 2012, and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. Provisional Patent Application No. 61/659,824, filed on Jun. 14, 2012, and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. Provisional Patent Application No. 61/664,387, filed on Jun. 26, 2012, and titled "SYSTEMS, COMPUTER MEDIUM AND COMPUTER-IMPLEMENTED METHODS FOR MONITORING HEALTH OF EMPLOYEES USING MOBILE DEVICES", and U.S. Provisional Patent Application No. 61/664,399, filed on Jun. 26, 2012, and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", the disclosures of which are each hereby incorporated by reference in their entireties.

FIELD OF INVENTION

The present invention relates generally to health monitoring and more particularly to systems, machines, non-transitory computer medium having computer program instructions stored thereon, and computer-implemented methods for monitoring the status of drivers of vehicles.

BACKGROUND OF THE INVENTION

When driving a vehicle, drivers expose themselves to the risk of being involved in an accident with other vehicles (e.g., a car crash). Such risks can be increased when drivers develop health conditions, such as fatigue or sleep deprivation that can lead to a vehicle accident. Unfortunately, the risks of driving a vehicle are not limited to car accidents. For example, while driving a vehicle, drivers with poor body position may increase their risks for developing physical health issues, such as neck pain, lower back pain, sciatic nerve issues, or the like. Accordingly, drivers may be exposed to a variety of risks when driving a vehicle.

Current measures for improving driver awareness of driving related safety and health issues include informing drivers about the associated risks. For example, campaigns for improving driver awareness of safety and health issues may simply include providing drivers with literature explaining the risks associated with driving and providing suggestion for reducing those risks. Such literature may explain the risks of driving when experiencing a health issue (e.g., fatigue) and the importance of being seated in an ergonomically correct body position to reduce the risks of developing physical health conditions (e.g., back pain due to poor ergonomics). Unfortunately, these techniques may not be effective. Although drivers may read the literature and intend to follow suggestions for reducing risks associated with driving, once behind the wheel of a vehicle, drivers tend to slip back into to old habits and simply forget to apply what they have learned. In some instances, the driver may not even be aware that they have a health issue or poor ergonomics that increase their risks for being involved in an accident or developing physical health issues. For example, a driver may not be aware that they are fatigued, that they are at risk for a health condition, or that they are seated in a non-ergonomic body position. As a result, despite the driver's desire to reduce their risks while driving, the driver may actually have an increased risk for being involved in a vehicle accidents and developing physical health issues based on conditions of which they are not aware.

SUMMARY OF THE INVENTION

Applicant has recognized several shortcomings of existing techniques for improving driver awareness of driving related safety and health issues, and, in view of these shortcomings, has recognized the need for a system for alerting drivers to health issues that may lead to an increased risk for vehicle accidents and/or alerting drivers to ergonomic issues that may lead to an increased risk for developing debilitating health issues such as neck pain, lower back pain, sciatic nerve issues, or the like. Applicant has recognized that although traditional methods of informing drivers may be provided, without monitoring of drivers and providing drivers with feedback to alert them to potential health issues and/or ergonomic issues, drivers often fail to engage in prudent driving habits. For example, without continual reminders regarding driver health and/or body position, drivers tend to slip into bad habits, such as poor body positioning in the driver's seat and driving while fatigued, that put driver at risk for vehicle accidents and health issues. Applicant has recognized that such shortcomings have failed to be addressed by others, and has recognized that such shortcomings may be addressed by a system that can identify current issues with a driver's health and body position, predict potential issues with a driver's health and body position, and provide corresponding feedback to the driver. Such a system may provide, for example, for reminding a driver to correct their body position to prevent physical injury before it occurs and/or provide for alerting a driver that they are fatigued and at risk for falling asleep when driving, thereby providing the driver the opportunity to bring the car to a stop and rest prior to the driver actually falling asleep while driving. In view of the foregoing, various embodiments of the present invention advantageously provide systems, machines, non-transitory computer medium having computer program instructions stored thereon, and computer-implemented methods for monitoring the health and ergonomic status of drivers when driving and providing feedback to the driver such that they are reminded to engage in safe and healthy driving habits.

In some embodiments, provided is a system for monitoring a status of a driver when driving a vehicle. The system including a driver status sensing system including a set of one or more driver status sensors configured to be disposed in the vehicle. The one or more driver status sensors including a set of one or more driver's seat sensors configured to output seat data indicative of a position of a head, a torso and a leg of the driver relative to a driver's seat of the vehicle, a set of one or more floorboard sensors configured to output floorboard data indicative of a position of feet of the driver relative to a floorboard of the vehicle, a set of one or more pedal sensors configured to output pedal data indicative of a position of feet of the driver relative to pedals of the vehicle, a set of one or more steering wheel sensors configured to output steering wheel data indicative of a position of hands of the driver relative to a steering wheel of the vehicle, a set of one or more rearview mirror sensors configured to output rearview mirror data indicative of a position of eyes of the driver relative to a rearview mirror of the vehicle, and a set of one or more brain sensors configured to output neural data indicative of a brain activity of the driver. The set of one or more driver status sensors configured to output driver status data corresponding to at least one of the seat data, the floorboard data, the pedal data, the steering wheel data, the rearview mirror data, and the neural data.

The system including a driver status processing system configured to receive the driver status data output by the set of one or more driver status sensors, process the driver status data to determine whether the driver is experiencing a health condition, process the driver status data to determine whether the driver is experiencing a health crisis, process the driver status data to determine whether a body position of the drive is ergonomically acceptable, in response to determining that the driver is experiencing a health condition, generating a health alert indicative of the health condition that is configured to be displayed to the driver via a display of a driver status feedback system, in response to determining that the driver is experiencing a health crisis generating a health alert indicative of the health crisis that is configured to be displayed to the driver via a display of the driver status feedback system and generate a command configured to cause inhibiting of operation of the vehicle, in response to determining that a body position of the drive is not ergonomically acceptable identify adjustments in the body position of the driver that need to be made for the driver to be positioned in a an ergonomically acceptable body position and generate an ergonomic alert indicative of adjustments in the body position of the driver that need to be made for the driver to be positioned in a an ergonomically acceptable body position that is configured to be displayed to the driver via a display of the driver status feedback system.

The driver status feedback system including the display, the display being configured to display, to the driver, the health alert indicative of the health condition, the health alert indicative of the health crisis and the ergonomic alert indicative of adjustments in the body position of the driver that need to be made for the driver to be positioned in a an ergonomically acceptable body position.

The step of processing the driver status data to determine whether a body position of the drive is ergonomically acceptable, in some embodiments, includes determining a current body position of the driver based at least in part on the driver status data received, identifying a target ergonomic body position, comparing the current body position of the driver to the target ergonomic body position identified, determining, based at least in part on the comparison, that a characteristic of the current body position of the driver does not satisfy a corresponding characteristic of the target ergonomic body position and determining that an adjustment needs to be made in the body position of the driver such that the characteristic of the current body position of the driver does satisfy the corresponding characteristic of the target ergonomic body position. Identify adjustments in the body position of the driver that need to be made for the driver to be positioned in a an ergonomically acceptable body position includes identifying the adjustment that needs to be made in the body position of the driver such that the characteristic of the current body position of the driver does satisfy the corresponding characteristic of the target ergonomic body position.

In some embodiments, the characteristic of the current body position includes contact of a head of the driver with a headrest, contact of a back of the driver with a seat-back, contact of a buttock/upper legs of the driver with a seat-bottom, contact of feet of the driver with a floorboard, contact of feet of the driver with a pedal, contact of hands of the driver with a steering wheel, an eye level of the driver, a back angle of the driver, an upper leg angle of the driver, a knee angle of the driver, a shoulder angle of the driver, an elbow angle of the driver, or a bottom/back force ratio of the driver.

In certain embodiments, the characteristic of the current body position of the driver includes a head position, a hand position, a back position or a foot position of the current body position of the driver.

In some embodiments, the driver status processing system is further configured to, in response to determining that a body position of the driver is not ergonomically acceptable, generate a move command configured to cause automatic movement of at least one of a driver's seat, pedals, a steering wheel or a rearview mirror of the vehicle to cause adjustments in the body position of the driver that need to be made for the driver to be positioned in a an ergonomically acceptable body position.

The driver status processing system is configured to, in some embodiments, continuously receive the driver status data, process the driver status data to determine whether the driver is experiencing a health condition, whether the driver is experiencing a health crisis and whether a body position of the drive is ergonomically acceptable such that the driver is provided with real-time feedback indicative of whether the driver is experiencing a health condition, whether the driver is experiencing a health crisis, and whether a body position of the drive is ergonomically acceptable.

In some embodiments, the health condition includes fatigue, and wherein the health alert indicative of the health condition includes a suggestion that the driver suspend driving the vehicle.

In certain embodiments, the command configured to cause inhibiting of operation of the vehicle includes a command configured to slow the vehicle to a stop.

In some embodiments, provided is a system for monitoring a status of a driver of a vehicle. The system including: a set of one or more ergonomic sensors configured to be disposed in the vehicle and configured to output ergonomics data corresponding to a current body position of the driver, an ergonomics processor configured to receive the ergonomics data output by the set of one or more ergonomic sensors, process the ergonomics data to identify an adjustment that needs to be made in the body position of the driver for the driver to be positioned in an ergonomic body position and generate ergonomic feedback content indicative of the adjustment in the body position of the driver that needs to be made for the driver to be positioned in the ergonomic body position, and a feedback display located in the vehicle, the feedback display being configured to display, to the driver when they are located in the vehicle, the ergonomics feedback content indicative of the adjustments in the body position of the driver that need to be made for the driver to be positioned in the ergonomic body position.

In certain embodiments, the ergonomics data is indicative of at least one of a head position, a hand position, a back position and a foot position the current body position of the driver.

The step of processing the ergonomic data to identify an adjustment that needs to be made in the body position of the driver for the driver to be positioned in an ergonomic body position, in some embodiments, includes determining a current body position of the driver based at least in part on the ergonomics data received, identifying an ergonomic body position, comparing the current body position of the driver to the ergonomic body position identified, determining, based at least in part on the comparison, that the current body position of the driver does not satisfy the ergonomic body position, and identifying adjustments in the body position of the driver that need to be made for the driver to be positioned in the ergonomic body position.

The step of determining based at least in part on the comparison that the current body position of the driver does not satisfy the ergonomic body position, in certain embodiments, includes determining that a characteristic of the current body position of the driver does not fall within an acceptable range for a corresponding characteristic of the ergonomic body position.

In some embodiments, the characteristic includes contact of a head of the driver with a headrest, contact of a back of the driver with a seat-back, contact of a buttock/upper legs of the driver with a seat-bottom, contact of feet of the driver with a floorboard, contact of feet of the driver with a pedal, contact of hands of the driver with a steering wheel, eye level of the driver, a back angle of the driver, an upper leg angle of the driver a knee angle of the driver, a shoulder angle of the driver, an elbow angle of the driver, or a bottom/back force ratio of the driver.

In certain embodiments, the characteristic include of a head position, a hand position, a back position or a foot position of the current body position of the driver.

In some embodiments, the driver status processing system is further configured to, in response to determining that a body position of the drive is not ergonomically acceptable, generate a move command to cause automatic movement of at least one of a driver's seat, pedals, a steering wheel and a rearview mirror of the vehicle to cause adjustments in the body position of the driver that need to be made for the driver to be positioned in a an ergonomically acceptable body position.

The ergonomics processor is configured to, in some embodiments, receive the ergonomic data, process the ergonomic data, and generate ergonomic feedback content when the user is driving the vehicle. The ergonomics feedback display, in some embodiments, is configured to display the ergonomics feedback content when the user is driving the vehicle such that the driver is informed, when driving, of adjustments that need to be made in the body position to achieve an ergonomic body position.

In some embodiments, the feedback content includes a suggestion for making adjustments in a position of at least one of a driver's seat, pedal, steering wheel or rearview mirror of the vehicle to achieve the ergonomic body position.

In certain embodiments, the system includes a set of one or more health sensors configured to be disposed in the vehicle and configured to output health data corresponding to a current health of the driver. The ergonomics processor configured to receive health data output by the set of one or more health sensors, process the health data to identify whether the driver is experiencing a health issue, and in response to determining that the driver is experiencing a health issue, generate health feedback content indicative of the health issue, wherein the health feedback content is configured to be displayed via the feedback display.

In some embodiments, the ergonomics processor is further configured to, in response to determining that the driver is experiencing a health issue, generate ergonomic feedback configured to automatically inhibit operation of the vehicle.

In certain embodiments, provided is a computer implemented method for providing monitoring ergonomics of a driver of a vehicle. The method including, receiving ergonomics data output by a set of one or more ergonomic sensors disposed in the vehicle and corresponding to a current body position of the driver, processing the ergonomic data to identify an adjustment that needs to be made in the body position of the driver for the driver to be positioned in an ergonomic body position, generating ergonomic feedback content indicative of the adjustments in the body position of the driver that need to be made for the driver to be positioned in the ergonomic body position, and displaying, via an ergonomics feedback display located in the vehicle. The ergonomics feedback content indicative of the adjustments in the body position of the driver that need to be made for the driver to be positioned in the ergonomic body position.

Accordingly, as described herein below, embodiments of the system, computer program instructions and associated computer-implemented methods for monitoring the status of drivers of vehicles and providing feedback corresponding thereto.

BRIEF DESCRIPTION OF THE DRAWINGS

So that the manner in which the features and advantages of the invention, as well as others, which will become apparent, may be understood in more detail, a more particular description of the invention briefly summarized above may be had by reference to the embodiments thereof, which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 10 is a block diagram that illustrates a driver monitoring system including components of a driver status feedback system in accordance with one or more embodiments of the present invention.

FIG. 11 is a flowchart that illustrates a method of monitoring the status of a driver of a vehicle in accordance with one or more embodiments of the present invention.

DETAILED DESCRIPTION

Figure 1:
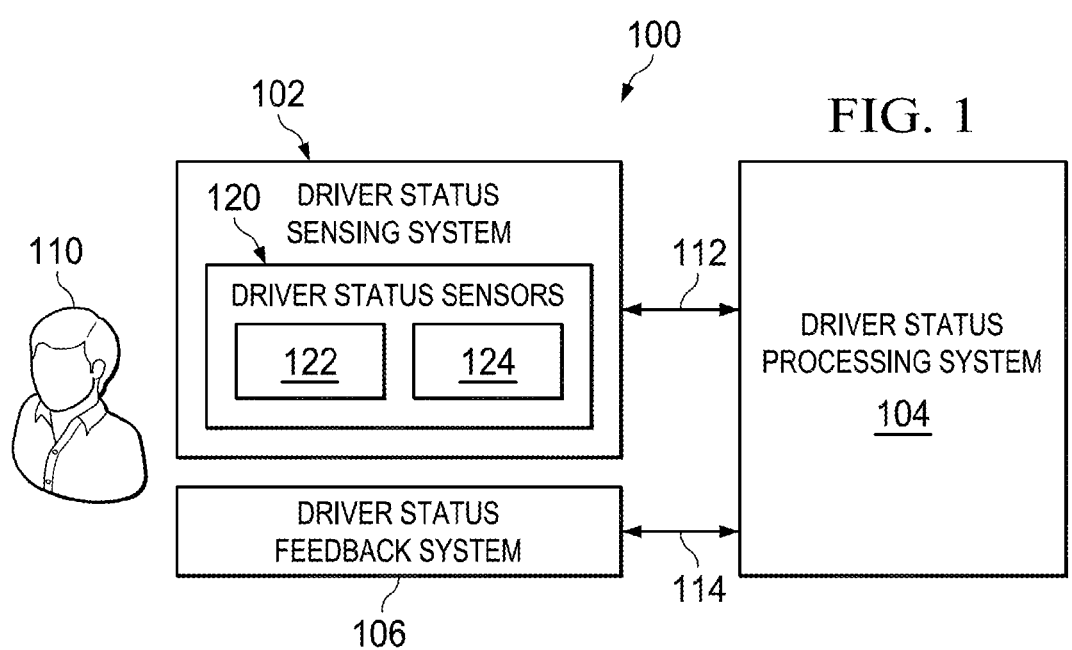
FIG. 1 is a block diagram that illustrates a driver monitoring system in accordance with one more embodiments of the present invention.

The present invention will now be described more fully hereinafter with reference to the accompanying drawings in which exemplary embodiments of the invention are shown. This invention may, however, be embodied in many different forms and should not be construed as limited to the illustrated embodiments set forth herein, rather, these exemplary embodiments are provided so that this disclosure will be thorough and complete, and will fully convey the scope of the invention to those skilled in the art.

As described in more detail below, provided is a driver monitoring system for monitoring the health and ergonomic status of a driver while they are seated in a driver's seat of a vehicle and/or driving the vehicle, and/or providing feedback regarding the health and ergonomic status of the driver. In some embodiments, the driver monitoring system includes sensors disposed throughout the environment surrounding the driver to measure various aspects of the driver's health and body position while seated in the driver's seat and/or driving the vehicle. In certain embodiments, sensors are integrated with the driver's seat, floorboard, pedals, steering wheel, rearview mirror and/or the like of the vehicle. In some embodiments, sensors worn by the driver, such as a headset for monitoring the brain activity of the driver, a heart rate monitor for monitoring the heart rate of the driver and/or the like.

In certain embodiments, data acquired via the sensors is used to assess the health and/or ergonomic status of the driver. In some embodiments, for example, the brain activity, heart rate and/or the like is used to determine whether the driver is experiencing a health condition, such as fatigue, a stroke, a heart-attack and/or the like. In certain embodiments, for example, location/force data received from the sensors is used to determine whether the driver's body position in the driver's seat is ergonomically acceptable.

In some embodiments, the driver is provided with an alert corresponding to issues revealed via assessment of the health and/or ergonomic status of the driver. In certain embodiments, for example, where it is determined that the driver has a health issue, a corresponding health alert (e.g., "You are fatigued. When possible, please stop operating the vehicle and do not drive until you have rested adequately") is displayed to the driver to alert them to the heath issue and/or provide suggestions for resolving the health issue. In some embodiments, for example, where it is determined that the driver has an ergonomic issue (e.g., their body position is not ergonomically correct/acceptable), a corresponding ergonomic alert is displayed (e.g., "Your body position is incorrect. Please move the driver's seat upward") to the driver to alert them to the ergonomic issue and/or provide suggestions for resolving the ergonomic issue.

In certain embodiments, actions are taken automatically to resolve identified issues. In some embodiments, for example, upon determining that the driver is experiencing a health crisis (e.g., has fallen asleep, is experiencing a stroke or heart-attack) operation of the vehicle is automatically inhibited (e.g., the vehicle is automatically slowed to a stop). In certain embodiments, for example, upon determining that the driver's body position is incorrect, the driver's seat, pedals, steering wheel, rearview mirror and/or the like may be automatically adjusted to correct the driver's body position such that it is ergonomically acceptable.

FIG. 1 is a block diagram that illustrates a driver monitoring system ("system") 100 in accordance with one more embodiments of the present invention. As depicted, system 100 may include driver status sensing system 102, a driver status processing system 104, and a driver status feedback system 106. As discussed herein system 100 may be employed to collect driver status data regarding the health and/or ergonomic status of a driver 110 when seated in and/or driving a vehicle, process the driver status data to assess/determine the driver's health and/or ergonomic status, and provide feedback to the driver regarding their health and/or ergonomic status. For example, driver status processing system 104 may be employed to collect (e.g., from driver status sensing system 102) driver status data 112 regarding the health and/or ergonomic status of driver 110 when seated in and/or driving a vehicle, process the driver status data to assess/determine the driver's health and/or ergonomic status, and/or provide (e.g., to driver status feedback system 106) driver status feedback 114 (e.g., driver status content for presentation to the driver regarding their current health and/or ergonomic status and/or commands for taking automated actions to resolve health and/or ergonomic issues identified).

In some embodiments, the collected driver status data may be used to assess a physical health of the driver to determine whether the driver is experiencing a health condition that may be unsuitable for driving and, if the driver is experiencing a health condition that may be unsuitable for driving, providing corresponding feedback. For example, where the collected health data indicates that the driver is suffering from fatigue, system 100 may provide the driver with an alert communicating to the driver that they should take a break from driving until they have rested for a sufficient period. Such a system may help to prevent vehicle accidents by alerting the driver to potential issues, such as falling asleep while driving, before they actually occur.

In some embodiments, the collected driver status data may be used to assess a body position of the driver to determine whether their driver's body position is ergonomically correct and providing feedback corresponding thereto. For example, where the driver status data collected indicates that the driver's body position is not ergonomically correct because the driver's seat is too low, system 100 may provide the driver with a suggestion to raise the driver's seat and/or may lower the driver's seat automatically to the suggested position. Such a system may help to prevent physical injuries by encouraging the driver to assume a proper ergonomic position that will help to prevent injuries that may otherwise occur if the driver were to continue to be seated in an ergonomically unacceptable position.

In some embodiments, driver status sensing system 102 includes one or more driver status sensors 120 that are employed to collect the driver status data relating the health and/or ergonomic status of the driver (e.g., driver health data and/or driver ergonomics data). In some embodiments, driver status sensors 120 include one or more health sensors 122 and/or ergonomic sensors ("body position sensors") 124. Health sensors 122 may include sensors that are used to collect health data indicative of biometric and/or biomechanic health characteristics of the driver. Ergonomic sensors 124 may include sensors that are used to collect ergonomic data indicative of the driver's body position when seated in a driver's seat of a vehicle. A sensor that is used to collect both of health data and ergonomic data may be referred to as an ergonomic/health sensor.

Figure 2:
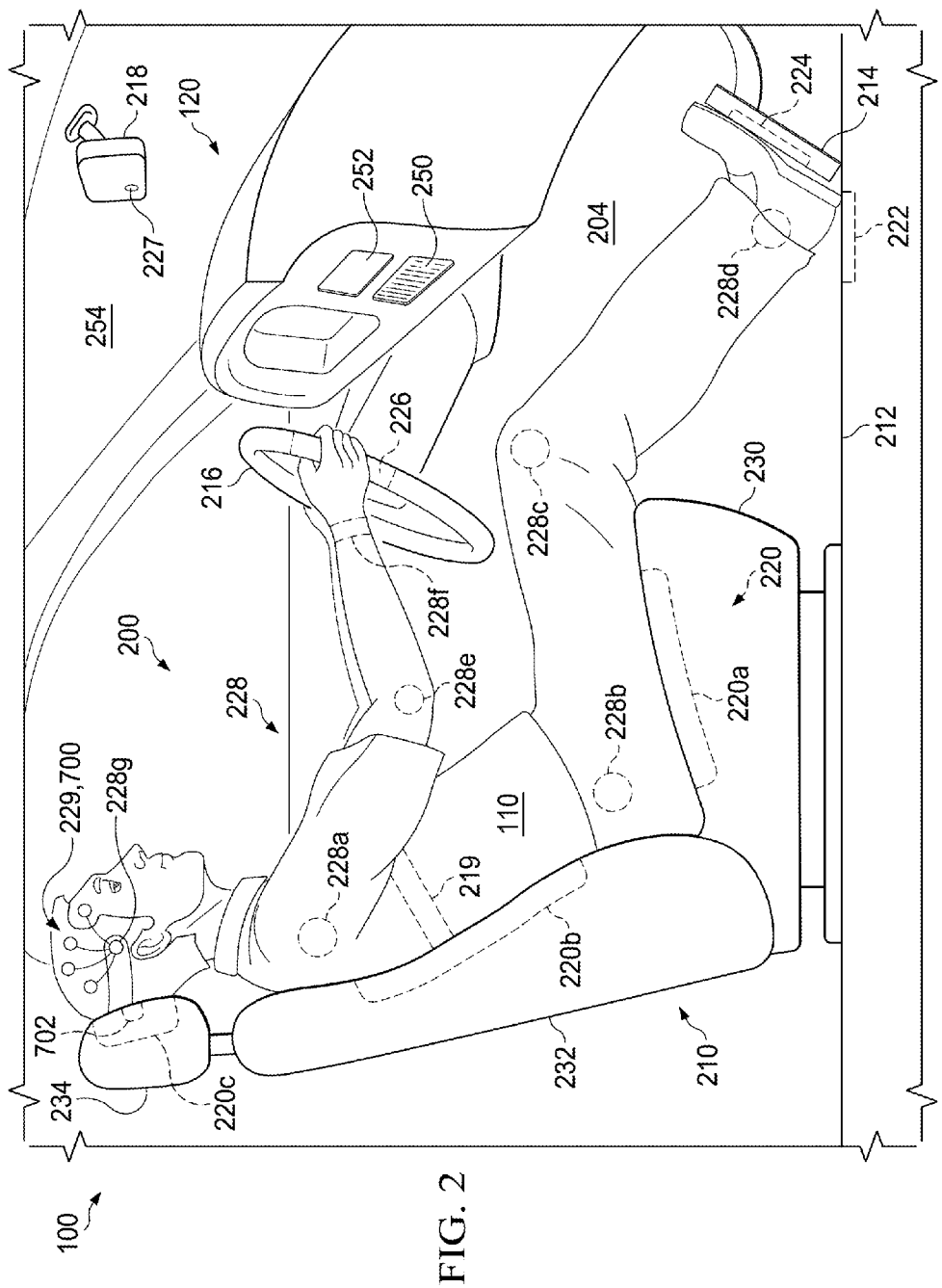
FIG. 2 illustrates an exemplary driver monitoring system including a status sensing system having a set of driver status sensors that are disposed throughout a driver environment of a vehicle in accordance with one more embodiments of the present invention.

FIG. 2 illustrates an exemplary driver monitoring system 100 including status sensing system 102 having a set of driver status sensors 120 that are disposed throughout a driver environment 200 of a vehicle 204 in accordance with one more embodiments of the present invention. Driver's environment 200 may include a region that immediately surrounds the driver when they are seated in driver's seat 210 of vehicle 204. For example, in the illustrated embodiment, driver's environment 200 includes a driver's seat 210, a floorboard 212, pedals 214, a steering wheel 216, and a rearview mirror 218. In some embodiments, set of driver status sensors 120 includes any combination of one or more of heart rate sensors 219, seat sensors 220, floorboard sensors 222, pedals sensors 224, steering wheel sensors 226, mirror sensors 227, body position sensors 228, and/or brain sensors 229.

Seat sensors 220 may include on or more sensors provided at driver's seat 210 for sensing the driver's body position when seated in driver's seat 210. For example, seat sensors 220 may include force and/or temperature transducers for sensing the positioning of the driver's buttocks and upper legs on a seat portion of driver's seat 210, sensing the positioning of the driver's back/torso against a back portion of driver's seat 210, and/or sensing the positioning of the driver's head against a headrest portion of driver's seat 210.

Figure 3:
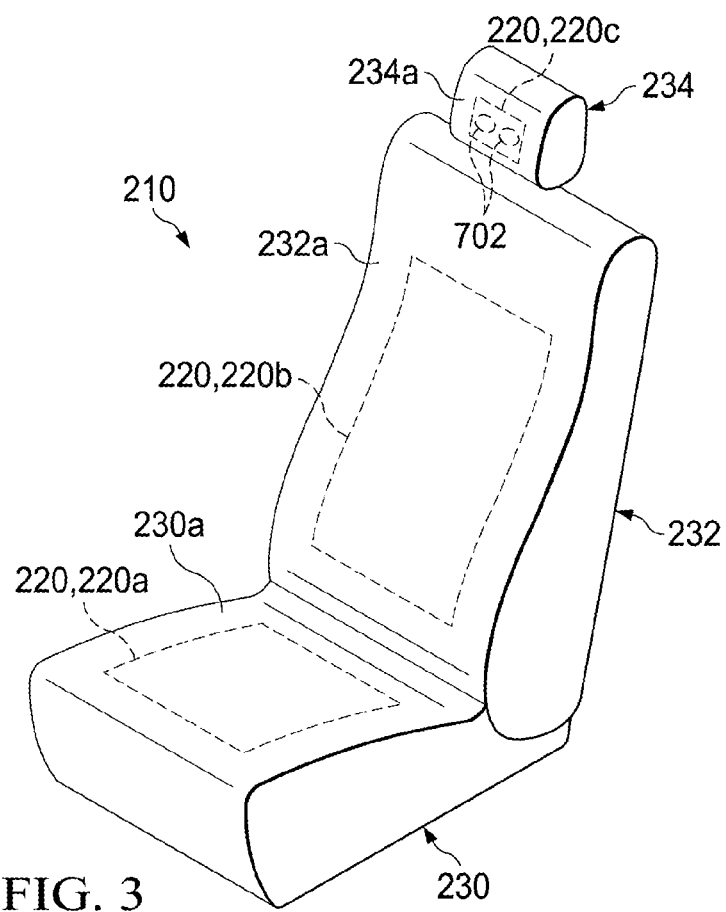
FIG. 3 illustrates a perspective view of a driver's seat in accordance with one or more embodiments of the present invention.

FIG. 3 illustrates a perspective view of driver's seat 210 including seat sensors 220 in accordance with one or more embodiments of the present invention. As depicted, driver's seat 210 may include a seat-bottom 230 and a seat-back 232. Seat-bottom 230 may include a lower portion of driver's seat 210 that is oriented substantially horizontally for supporting the driver's buttocks and/or upper-legs when the driver is seated in seat 210. Seat-bottom 230 may include an upper-seating surface 230a, that contacts and supports the driver's buttocks and upper-legs when the driver is seated in driver's seat 210.

In some embodiments, seat-bottom 230 includes a seat sensor 220 disposed thereon. For example, seat-bottom 230 may include a seat-bottom sensor 220a, disposed on upper-seating surface 230a, for sensing the positioning of the driver's buttocks and upper legs on upper-seating surface 230a, of seat-bottom 230 when the driver is seated in driver's seat 210. In some embodiments, seat-bottom sensor 220a, is integrated within upper-seating surface 230a. For example, seat-bottom sensor 220a, may be provided directly underneath upper-seating surface 230a, of seat-bottom 230. In some embodiments, seat-bottom sensor 220a, is integrated within a cover/pad provided on upper-seating surface 230a. For example, seat-bottom sensor 220a, may be provided in a seat cover/pad that is disposed on top of upper-seating surface 230a, of seat-bottom 230. In some embodiments, seat-bottom sensor 220a, includes a force sensor that outputs seat-bottom sensor data that is indicative of the driver's positioning in driver's seat 210. For example, where seat-bottom sensor 220a, includes a force sensor, seat-bottom sensor data may be indicative of a force of the driver's buttock and/or upper legs exerted on upper seat surface 230a. In some embodiments, seat-bottom sensor 220a, includes a position sensor (e.g., a gyro) that outputs seat-bottom sensor data that is indicative of an orientation of the seat-bottom 230 of driver's seat 210. For example, where seat-bottom sensor 220a, includes a gyro sensor, seat-bottom sensor data may be indicative of an angle of upper seat surface 230a, relative to horizontal.

Seat-back 232 may include an upper portion of driver's seat 210 that is oriented substantially vertically for supporting the driver's back/torso/head when the driver is seated in seat 210. Seat-back 232 may include a back-support surface 232a, that contacts and supports the driver's back/torso when the driver is seated in driver's seat 210.

In some embodiments, seat-back 232 includes a seat sensor 220 disposed thereon. For example, seat-back 232 may include a seat-back sensor 220b, disposed on back-support surface 232a, for sensing the positioning of the driver's back/torso against back-support surface 232a when the driver is seated in driver's seat 210. In some embodiments, seat-back sensor 220b, is integrated within back-support surface 232a. For example, seat-back sensor 220b, may be provided directly underneath back-support surface 232a, of seat-back 232. In some embodiments, seat-back sensor 220b, is integrated within a cover/pad provided on back-support surface 232a. For example, seat-back sensor 220b, may be provided in a seat cover/pad that is disposed over back-support surface 232a, of seat-back 232. In some embodiments, seat-back sensor 220b includes a force sensor that outputs seat-back sensor data that is indicative of the driver's positioning in driver's seat 210. For example, where seat-back sensor 220b, includes a force sensor, seat-back sensor data may be indicative of a force of the driver's back/torso exerted against back-support surface 232a. In some embodiments, seat-back sensor 220b, includes a position sensor (e.g., a gyro) that outputs seat-back sensor data that is indicative of an orientation of seat-back 232 of driver's seat 210. For example, where seat-back sensor 220b, includes a gyro sensor, seat-back sensor data may be indicative of an angle of back-seat surface 232a, relative to vertical.

In some embodiments, seat-back 232 includes a headrest 234. Headrest 234 may be disposed at an upper-end of seat-back 232 for supporting the driver's head when the driver is seated in seat 210. Headrest 234 may include a head-support surface 234a, that contacts and supports the backside of the driver's head when the driver is seated in driver's seat 210.

In some embodiments, headrest 234 includes a seat sensor 220 disposed thereon. For example, headrest 234 may include a headrest sensor 220c, disposed on head-support surface 234a, for sensing the positioning of the driver's head against head-support surface 234a, when the driver is seated in driver's seat 210. In some embodiments, headrest sensor 220c, is integrated within head-support surface 234a. For example, headrest sensor 220c, may be provided directly underneath head-support surface 234a, of headrest 234. In some embodiments, headrest sensor 220c, is integrated within a cover/pad provided on head-support surface 234a. For example, headrest sensor 220c, may be provided in a headrest cover/pad that is disposed over head-support surface 234a, of headrest 234. In some embodiments, headrest sensor 220c, includes a force sensor that outputs headrest sensor data that is indicative of the driver's positioning in driver's seat 210. For example, where headrest sensor 220c, includes a force sensor, headrest sensor data may be indicative of a force of the driver's head exerted against head-support surface 234a. In some embodiments, headrest sensor 220c, includes a position sensor (e.g., a gyro) that outputs headrest sensor data that is indicative of an orientation of head-support surface 234a, of headrest 234. For example, where headrest sensor 220c, includes a gyro sensor, headrest sensor data may be indicative of an angle of head-support surface 234a, relative to vertical.

In some embodiments, seat 210 is adjustable to accommodate various driving positions. For example, seat-bottom 230 may be slid forward (e.g., toward steering wheel 136) of backwards (e.g., away from steering wheel 216) to move the entirety of seat 210 forward or backwards. Seat-bottom 230 may be raised or lowered to raise or lower the entirety of seat 210. Seat-bottom 230 may be tilted forward (e.g., rotated clockwise in FIG. 2) or backward (e.g., rotated counter-clockwise in FIG. 2) to tilt the entirety of driver's seat 210 forward or backward. Seat-back 232 may be tilted forward (e.g., rotated clockwise in FIG. 2) or backward (e.g., rotated counter-clockwise in FIG. 2) to adjust the angle of support for the driver's back/torso/head. Headrest 234 may be extended upward (e.g., away from a top of seat-back 232) or retracted downward (e.g., toward seat-back 232) to adjust a height for supporting the driver's head. Head-rest 234 may be tilted forward (e.g., rotated clockwise in FIG. 2) or backward (e.g., rotated counter-clockwise in FIG. 2) to adjust the angle of support for the driver's head.

In some embodiments, adjustments to seat position may be provided manually. For example, adjustments to the position of driver's seat 210 may include the driver pulling on levers and exerting manual force to slide, tilt, or otherwise adjust the various portions of driver's seat 210. In some embodiments, adjustments to seat position may be provided manually with assistance. For example, adjustments to the position of driver's seat 210 may include the driver pressing directional buttons that cause motors or similar positing devices to slide, tilt, or otherwise adjust the various portions of driver's seat 210. In some embodiments, adjustments to seat position may be provided automatically (e.g., with little to no user interaction). For example, adjustments to the position of driver's seat 210 may include motors (or similar positing devices) that are employed to automatically slide, tilt, or otherwise adjust the various portions of driver's seat 210. Such automatic adjustments may be implemented where, for example, the driver has a preferred seating potion that is pre-stored, and driver's seat 210 is automatically adjusted to the preferred seating position upon determining that the driver is seated in driver's seat 210 and/or a selection is made to return driver's seat 210 to the preferred seating position (e.g., the driver or another driver selecting a button to return the seat in the preferred seating position). In some embodiments, automatic adjustments may be implemented to make adjustments to the position of the driver's seat to correct the driver's body position such that it is ergonomically acceptable.

Figure 4:
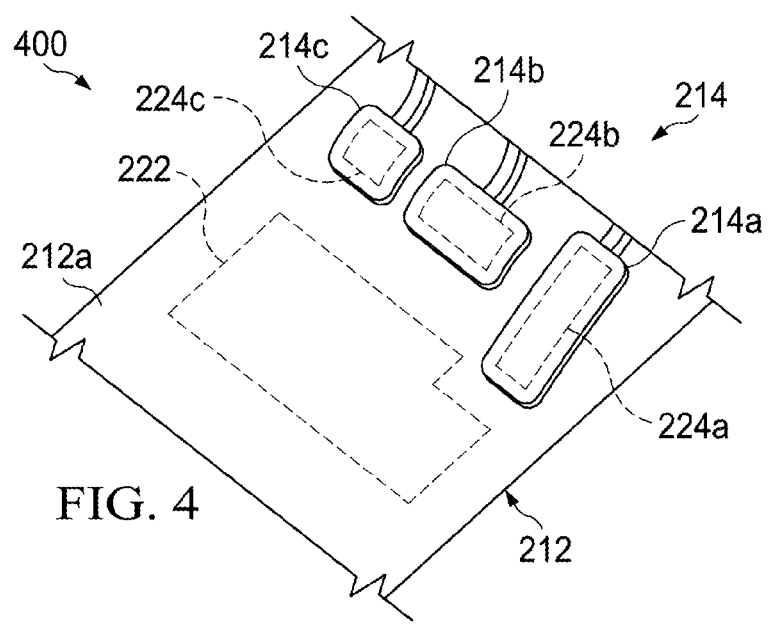
FIG. 4 illustrates a perspective view of a floor region of the vehicle in accordance with one or more embodiments of the present invention.

FIG. 4 illustrates a perspective view of a floor region 400 of vehicle 204 in accordance with one or more embodiments of the present invention. In some embodiments, floorboard 212 includes a lower/floor surface of the vehicle where the driver's feet are typically located when driving. Floorboard 212 may include a substantially horizontally oriented upper surface 212a, that is located under and adjacent pedals 214 for supporting the driver's feet. For example, the driver may rest a heel of their right foot on floorboard 212 while the ball of the foot is used to engage (e.g., press down on) a gas or brake pedal (see FIG. 2) and/or the driver may rest a heel of their left foot on upper surface 212a, of floorboard 212 while the ball of the foot is used to engage (e.g. press down on) a clutch pedal. The driver may rest their feet on upper surface 212a, of floorboard 212 when they are not engaging one of pedals 214. In some embodiments, upper surface 212a, of floorboard 132 includes a floor mat disposed thereon for protecting floorboard 212 from wear and tear caused by the driver resting their feet on floorboard 212 and/or debris that may be carried into the vehicle via the driver's footwear.

In some embodiments, floorboard 212 includes a floorboard sensor 222 provided thereon. For example, floorboard 212 may include floorboard sensor 222 disposed on upper surface 212a, for sensing the positioning of the driver's feet on upper surface 212a, of floorboard 212 when the driver is seated in driver's seat 210. In some embodiments, floorboard sensor 222 is integrated within floorboard upper surface 212a. For example, floorboard sensor 222 may be provided directly on or directly underneath upper surface 212a, of floorboard 222. In some embodiments, floorboard sensor 222 is integrated within a mat provided on upper surface 212a. For example, floorboard sensor 222 may be integrated with a floor mat that is disposed on top of upper surface 212a, of floorboard 212.

In some embodiments, floorboard sensor 222 includes a force sensor that outputs floorboard sensor data that is indicative of the positioning of the driver's feet. For example, where floorboard sensor 222 includes a force sensor, floorboard sensor data may be indicative of a force of the driver's feet (e.g., heels) exerted on upper surface 212a. Such floorboard sensor data may be used to determine that the driver's feet are contacting floorboard 212.

In some embodiments, pedals 214 include an accelerator pedal ("gas pedal") 214a,, a broke pedal 214b,, and/or a clutch pedal 214c. The driver may depress the gas pedal 214a, with their foot to cause the vehicle to accelerate. The driver may depress the brake pedal 214b, with their foot to cause the vehicle to decelerate (e.g., stop). The driver may depress the clutch pedal 214c, with their foot to enable shifting of gears in a manual transmission and/or to regulate torque output by the vehicle. In some embodiments, gas pedal 214a,, brake pedal 214b, and/or clutch pedal 214c, include a gas pedal sensor 224a,, a brake pedal sensor 224b, and/or a clutch pedal sensor 224c,, respectively. The pedal sensors 224 may be disposed on a surface of the pedals for detecting when the driver's foot has engaged (e.g., is contacting) the respective pedals.

In some embodiments, each of pedal sensors 224 includes a force sensor that outputs pedal sensor data that is indicative of whether the driver's feet are engaging (e.g., contacting) pedals 214. For example, where gas pedal sensor 224a,, a brake pedal sensor 224b, and/or a clutch pedal sensor 224c, each includes a force sensor, pedal sensor data may include gas pedal sensor data indicative of a force of the driver's foot exerted on gas pedal 214a,, brake pedal sensor data indicative of a force of the driver's foot exerted on brake pedal 214b,, and/or clutch pedal sensor data indicative of a force of the driver's foot exerted on clutch pedal 214c,, respectively. Such pedal sensor data may be used to determine that the driver's feet are contacting pedals 214.

Figure 5:
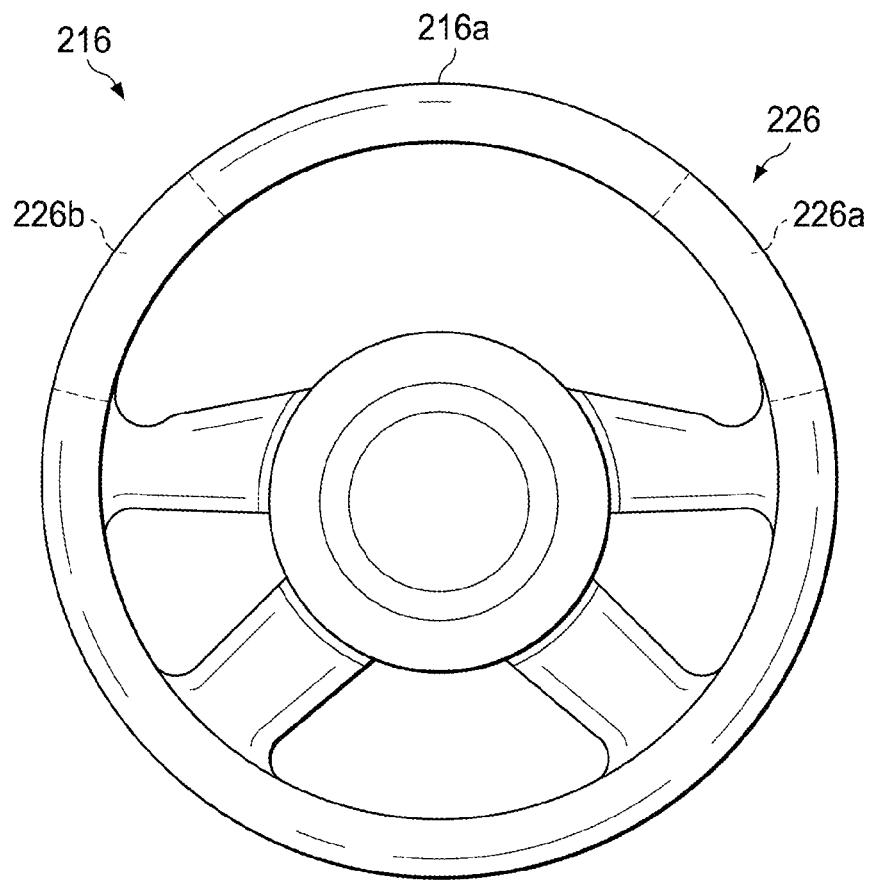
FIG. 5 illustrates a front view of a steering wheel of the vehicle in accordance with one or more embodiments of the present invention.

FIG. 5 illustrates a front view of steering wheel 216 of vehicle 204 in accordance with one or more embodiments of the present invention. In some embodiments, steering wheel 216 includes a device that can be manipulated by the driver to steer the vehicle in a desired direction. In some embodiments, steering wheel 216 includes a steering wheel sensor 226. For example, steering wheel 216 may include steering wheel sensor 226 disposed on a body 216a, of steering wheel 216 for sensing the positioning of the driver's hands on body 216a, of steering wheel 216. In some embodiments, steering wheel sensor 226 is integrated within body 216a. For example, steering wheel sensor 226 may be provided directly on or directly underneath an exterior surface of body 216a. In some embodiments, steering wheel sensor 226 is integrated within a cover provided on body 216a, of steering wheel 216. For example, steering wheel sensor 226 may be integrated with a steering wheel cover that is disposed over body 216a, of steering wheel 216. In some embodiments, steering wheel sensor 226 includes one or more sensors disposed at various locations about body 216a, of steering wheel 216 for detecting the driver's hand position on steering wheel 216. For example, right and left steering wheel sensors 226a, and 226b, may be provided at the "2, o'clock" and "10, o'clock" positions, respectively, on body 216a, of steering wheel 216 such that the positioning of the driver's hand at the "2, o'clock" and "10, o'clock" positions can be detected. Other embodiments may include positioning of steering wheel sensors 226 in any variety of suitable positions for detecting the driver's hand position on body 216a, of steering wheel 216.

In some embodiments, steering wheel sensors 226 include force sensors that output steering wheel sensor data that is indicative of the positioning of the driver's hands on body 216a of steering wheel 216. For example, where right and left steering wheel sensors 226a, and 226b each include a force sensor, steering wheel sensor data may include right steering wheel sensor data indicative of a force of the driver's right hand exerted on steering wheel sensor 226a, and/or left steering wheel sensor data indicative of a force of the driver's left hand exerted on steering wheel sensor 226b. Such steering wheel sensor data may be used to determine that the driver's hands are contacting steering wheel 216 at the "2, o'clock" and "10, o'clock" positions.

Figure 6:
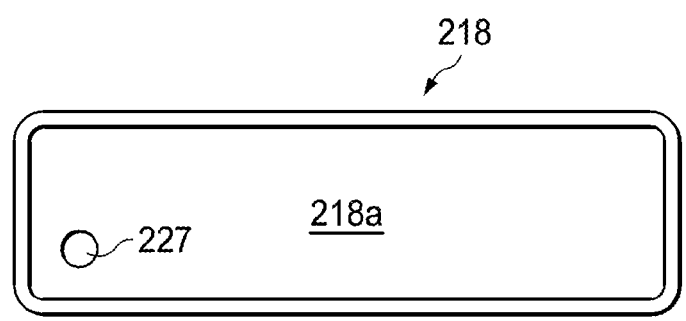
FIG. 6 illustrates a front view of a rearview mirror of the vehicle in accordance with one or more embodiments of the present invention.

FIG. 6 illustrates a front view of rearview mirror 218 of vehicle 204 in accordance with one or more embodiments of the present invention. In some embodiments, rearview mirror 218 includes a mirrored surface 218a, that enables the user to see rearward of the vehicle. Rearview mirror 218 may be located at or near the upper/center portion of a front windshield of vehicle 204 such that the driver may simply gaze upward to see a reflection of what is located to the rear of the vehicle (e.g., other cars following the vehicle). In some embodiments, rearview mirror 218 includes a rearview mirror sensor 227 disposed therein. For example, rearview mirror 218 may include a camera for sensing the driver's body position and/or eye position. In some embodiments, the camera includes a two-dimensional ("2D") or three-dimensional ("3D") camera having a field of view of some or all of the driver's body when seated in driver's seat 210. The camera may be used to capture images (e.g., 2D and/or 3D video and/or still images) that can be used to determine the driver's body position (e.g., the position of the driver's head, torso, waist, legs, feet, arms, hands, and/or the like) and eye position (e.g., including the direction in which the user is looking).

In some embodiments, rearview mirror sensor 227 outputs rearview mirror sensor data that is indicative of the driver's body and/or eye position. For example, where rearview mirror sensor 227 includes a camera, the rearview mirror sensor data may include image data (e.g., 2D and/or 3D video and/or still images) that is indicative of the driver's body position (e.g., the position of the driver's head, torso, waist, legs, feet, arms, hands, and/or the like) and/or eye position (e.g., including the direction in which the user is looking). In some embodiments, rearview mirror sensor 227 includes a device such as the Kinect™ manufactured by Microsoft. Such a 3D camera may include a software development kit that provides for employing the camera as a biomechanical sensor for determining various biometric aspects of the employee, including body position.

In some embodiments, position sensors 228 include a set of one or more positioning devices (e.g., RFID sensors) that can be used to locate a relative or absolute position of various portions of the driver's body. For example, as depicted (see FIG. 2), position sensors 228 may include shoulder position sensors 228a, located at or near the driver's right and left shoulder joints, hip position sensors 228b, located at or near the driver's right and left hip joints, knee position sensors 228c, located at or near the driver's right and left knee joints, ankle/foot position sensors 228d, located at or near the driver's right and left ankle joints, elbow position sensors 228e, located at or near the driver's right and left elbow joints, hand/wrist position sensors 228f located at or near the driver's right and left wrists, and/or head position sensors 228g, located at or near the driver's right and left ears such that a location/position of the employee's shoulders, hip, knees, ankles/feet, elbows, wrists/hands, head/ears and/or the like can be determined.

In some embodiments, each of position sensors 228 output position sensor data that is indicative of their respective location. For example, where position sensors 228 includes shoulder position sensors 228a,, hip position sensors 228b,, knee position sensors 228c,, ankle/foot position sensors 228d,, elbow position sensors 228e,, hand/wrist position sensors 228f,, and/or head position sensors 228g,, the position sensor data may include coordinates (e.g., 3D coordinates) indicative the location (e.g., in three-dimensional space) of the driver's shoulders, hip, knees, ankles/feet, elbows, wrists/hands and/or head as provided by corresponding ones of the sensors 228. As will be appreciated by those skilled in the art, such position sensor data may be used to determine locations of the corresponding portions of the driver's body and, thus, driver's body position. For example, shoulder position data output by shoulder position sensors 228a, may be indicative of the locations of the driver's shoulders and, thus, can be used to determine the location of the driver's shoulders. Similar position data may be provided by each of position sensors 228 (e.g., 228a-228g) and processed to determine locations corresponding thereto.

In some embodiments, brain sensor 229 includes a plurality of neural sensors for sensing brain activity (e.g., neural activity) of the driver. A neural sensor may include an electrode for sensing brain activity of the driver. In some embodiments, neural sensors may employ electroencephalography ("EEG") to measure neuro-signal voltage fluctuations resulting from ionic current flows within the neurons of the brain. EEG may refer to recording of the brain's spontaneous electrical activity over a short period of time (e.g., twenty to forty minutes) from a plurality of neural sensors disposed on the employee's scalp. For example, a plurality of neural sensor (e.g., sixteen neural sensors/channels) may be disposed about the employee's scalp to detect neuro-signals (e.g., including alpha, beta, gamma, and delta waves) that can be used to determine the employee's brain state, including their emotional state (e.g., distracted, angry happy, sad, excited, etc.), thoughts (e.g., cognitive thoughts, subconscious thoughts, intent, etc.), facial movements (e.g., facial expressions), motor functions and/or the like. Such data can be used to determine wither the driver is fatigued/tired (e.g., suffering from sleep deprivation), and/or the like.

Figure 7:
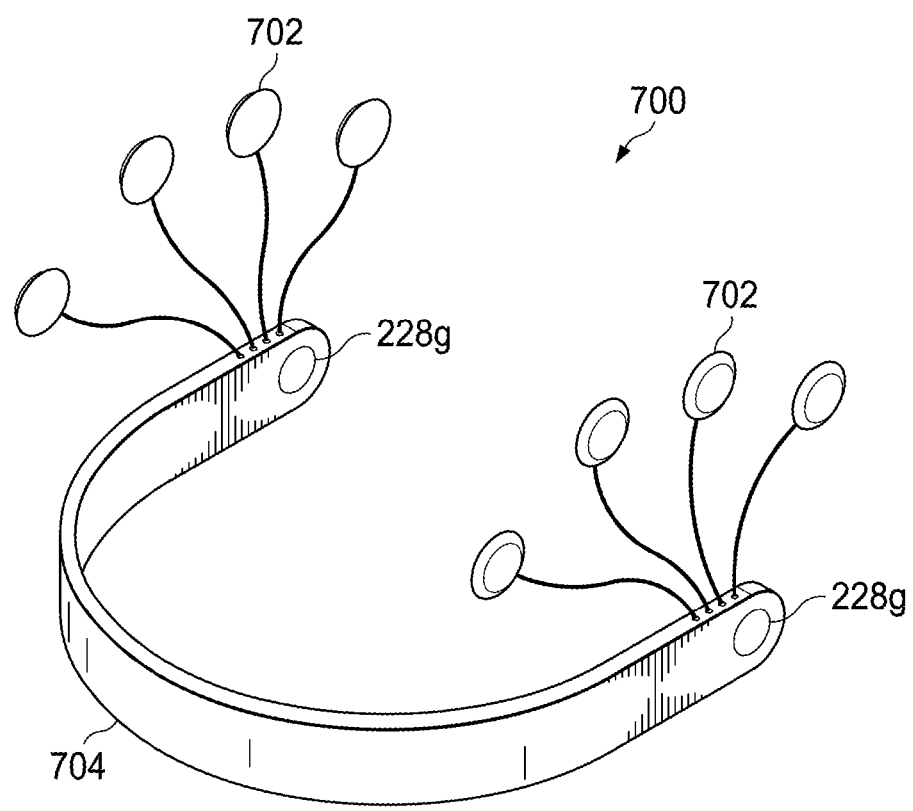
FIG. 7 is a perspective view of a neuro-headset including a plurality of neural sensors in accordance with one or more embodiments of the present invention.

FIG. 7 is a perspective view of a neuro-headset 700 including a plurality of neural sensors 702 in accordance with one or more embodiments of the present invention. Neuro-headset may be worn on the driver's head when seated in driver's seat 210 (see FIG. 2). Neuro-headset 700 may include a neuro-headset frame 704 having a plurality of neural sensors 702 (e.g., sixteen neural sensors 702) coupled thereto. Neuro-headset frame 704 may provide for positioning of the neural sensors 218 in discrete neural sensor locations about the driver's head. In some embodiments, one or more head positioning devices 228g, may be integrated with neuro-headset 700 such that a head positioning device 228g, is disposed about the driver's head when neuro-headset 700 is being worn by the driver. For example, head positioning devices 228g, may be located on a portion of headset 700 to be positioned near the side (e.g., both ears), front and/or back of the driver's head.

In some embodiments, brain sensors 229 output brain sensor data (e.g., neural sensor data) that is indicative of the brain activity of the driver. For example, where brain sensors 229 include neural sensors 702, neural sensors 702 may output neural sensor data indicative of detected neuro-signals (e.g., including alpha, beta, gamma, and delta waves) that can be used to determine the employee's brain state/activity, including their emotional state (e.g., happy, sad, excited, etc.), thoughts (e.g., cognitive thoughts, subconscious thoughts, intent, etc.), facial movements (e.g., facial expressions), motor functions and/or the like.

In some embodiments, brain sensors 229 are provided in a surface that supports or otherwise contacts the head of driver 110 while seated in driver's seat 210. For example, headrest 234 may include one or more neural sensors 702 disposed on head-support surface 234a, (see FIGS. 2 and 3). Neural sensors 702 may contact the back of the driver's head while they are seated in driver's seat 210, enabling the one or more neural sensors to sense the brain activity of driver 110 when the driver is seated in driver's seat 210. In some embodiments, neural sensors 702 include dry electrodes that can be used to sense neuro signals when in contact with the driver's scalp. Such dry electrodes may require minimal or no skin preparation for disposing the contact of the electrode on the employee's scalp. In some embodiments, one or more neural sensors 702 are integrated within head-support surface 234a. For example, one or more neural sensors 702 may be provided directly underneath head-support surface 234a, of headrest 234. In some embodiments, one or more neural sensors 702 are integrated within a cover/pad provided on head-support surface 234a. For example, one or more neural sensors 702 may be provided in a headrest cover/pad that is disposed over head-support surface 234a, of headrest 234.

In some embodiments, a heart rate sensor 219 (see FIG. 2) outputs heart rate data 112h indicative of the driver's heart rate sensed by heart rate sensor 219 (e.g., 80, beats per minute ("BPM")). Heart rate sensor 219 may include a heart rate monitor is positioned about the employee's torso (e.g., a heart rate monitor strapped about the driver's chest).

In some embodiments, driver's environment 200 includes one or more devices for presenting information to the driver regarding their status. For example, driver's environment may include a display device 250 and/or an audio device 252 for displaying and/or audibly presenting information to the driver. In some embodiments, display device 250 includes a graphical display for displaying driver status information. For example, display device may include a display provided in the dash of vehicle 204 (e.g., a display screen of a radio device, navigation device, the instrument/gauge cluster, and/or the like), a head-up display (e.g., a display that projects images onto a windshield 254 of vehicle 204 such that the images are reflected for viewing by the driver and appear as an overlay in the driver's field of view through the windshield), and/or the like. In some embodiments, audio device 252 includes a speaker for presenting status information audibly to the driver. For example, audio device 252 may include speakers of a stereo system of the vehicle, of an integrated phone system of the vehicle, or the like.

Figure 8:
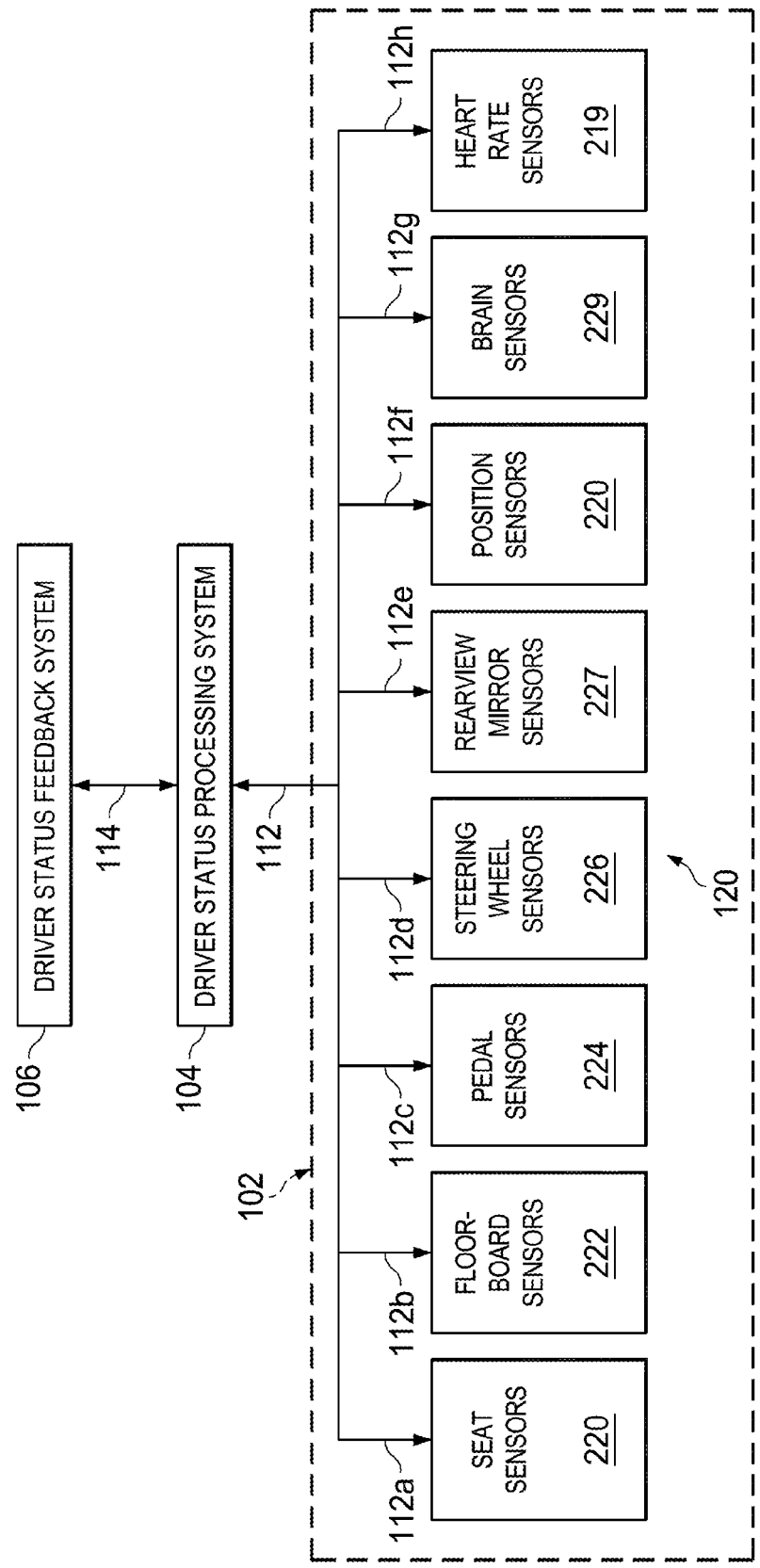
FIG. 8 is a block diagram that illustrates a driver monitoring system including components of a driver status sensing system in accordance with one or more embodiments of the present invention.

FIG. 8 is a block diagram that illustrates driver monitoring system 100 including components of driver status sensing system 102 in accordance with one or more embodiments of the present invention. In some embodiments, driver status sensing system 102 includes a plurality of driver status sensors 120 communicatively coupled to driver status processing system 104 and/or driver status processing system 104 is communicatively coupled to driver status feedback system 106.

Driver status sensors 120 may include seat sensors 220 (e.g., seat-bottom sensor 220a, seat-back sensor 220b,, and/or headrest sensor 220c), floorboard sensors 222, pedal sensors 224 (e.g., gas pedal sensor 224a,, brake pedal sensor 224b, and/or clutch pedal sensor 224c), steering wheel sensors 226 (e.g., right steering wheel sensor 226a, and/or left steering wheel sensor 226b), rearview mirror sensors 227, position sensors 228 (e.g., shoulder position sensors 228a,, hip position sensors 228b,, knee position sensors 228c,, ankle/foot position sensors 228d,, elbow position sensors 228e,, hand/wrist position sensors 228f,, and/or head position sensors 228g), and/or brain sensors 229 (e.g., neural sensors). Driver status processing system 104 may collect driver status data 112 from driver status sensors 120. In some embodiments, driver status data 112 includes sensor data collected from the respective sensors 120. Driver status data 112 may include seat sensor data 112a, (e.g., including seat-bottom sensor data, seat-back sensor data, and/or headrest sensor data) collected from seat sensors 220 (e.g., seat-bottom sensor 220a,, seat-back sensor 220b,, and/or headrest sensor 220c), floorboard sensor data 112b, collected from floorboard sensors 222, pedal sensor data 112c, (e.g., including gas pedal sensor data, brake pedal sensor data, and/or clutch pedal sensor data) collected from pedal sensors 224 (e.g., gas pedal sensor 224a,, brake pedal sensor 224b, and/or clutch pedal sensor 224c), steering wheel sensor data 112d, (e.g., right steering wheel sensor data and/or left steering wheel sensor data) collected from steering wheel sensors 226 (e.g., right steering wheel sensor 226a, and/or left steering wheel sensor 226b), rearview mirror sensor data 112e, collected from rearview mirror sensors 227, position sensor data 112f, (e.g., shoulder position sensor data, hip position sensor data, knee position sensor data, ankle/foot position sensor data, elbow position sensor data, hand/wrist position sensor data, and/or head position sensor data) collected from position sensors 228 (e.g., shoulder position sensors 228a,, hip position sensors 228b,, knee position sensors 228c,, ankle/foot position sensors 228d,, elbow position sensors 228e,, hand/wrist position sensors 228f,, and/or head position sensors 228g), brain/neural sensor data 112g, collected from brain sensors 229 (e.g., neural sensors 229a) and/or heart rate data 112h, collected from heart rate sensor 219.

In some embodiments, sensors 120 are communicatively coupled to driver status processing system 104 via a wired connection. For example, some or all of sensors 120 may include a communication cable extending between each of the respective sensors driver status processing system 104. In some embodiments, sensors 120 are communicatively coupled to driver status processing system 104 via a wireless connection. For example, some or all of sensors 120 may communicate with driver status processing system 104 via a wireless connection such as a Bluetooth connection and/or the like. In some embodiments, driver status data 112 is transmitted from the respective sensors 120 to driver status processing system 104 via the wired or wireless connections.

Figure 9:
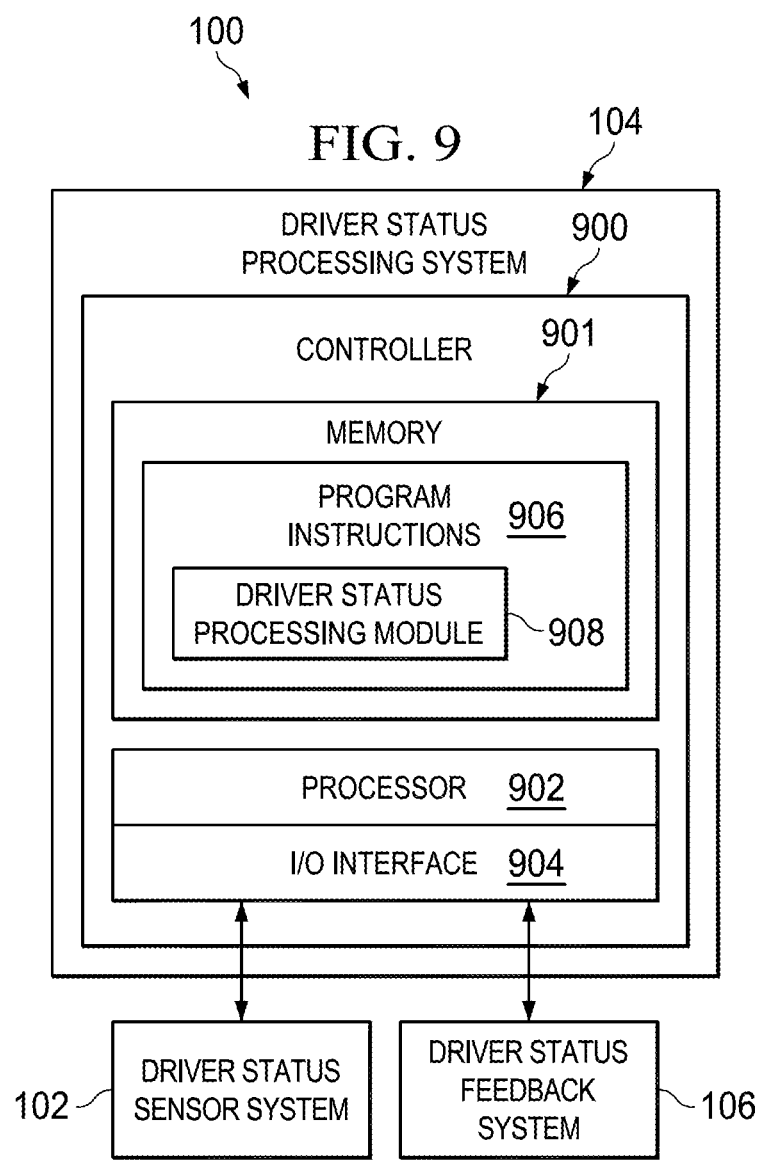
FIG. 9 is a block diagram that illustrates a driver monitoring system including components of a driver status processing system in accordance with one or more embodiments of the present invention.

FIG. 9 is a block diagram that illustrates driver monitoring system 100 including components of driver status processing system 104 in accordance with one or more embodiments of the present invention. In some embodiments, driver status processing system 104 includes a controller 900 for controlling the operational aspects of driver status processing system 104. For example, controller 900 may provide for collecting driver status data 112 from the various sensors 120 of driver status sensing system 102, processing the collected driver status data 112 and/or providing driver status feedback 114 to driver status feedback system 106. In some embodiments, controller 900 includes a memory 901, a processor 902 and an input/output (I/O) interface 904.

Memory 901 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. Memory 901 may include a non-transitory computer readable storage medium having program instructions 906 stored thereon that are executable by a processor (e.g., processor 902) to cause the functional operations (e.g., methods/routines/processes) described herein with regard to driver status processing system 104. Program instructions 906 may include a driver status processing module 908 including program instructions that are executable by processor 902 to provide some or all of the functionality described herein with regard to driver status processing system 104.

Processor 902 may be any suitable processor capable of executing/performing program instructions. Processor 902 may include a central processing unit (CPU) that carries out program instructions (e.g., of driver status processing module 908) to perform arithmetical, logical, and input/output operations of driver status processing system 104, including those described herein.

I/O interface 904 may provide an interface for connection of one or more I/O devices to driver status processing system 104. I/O devices may include driver status sensor system 102 (e.g., sensors 120), driver status feedback system 106 (e.g., a display device), a network server, and/or the like. I/O devices may be connected to I/O interface 904 via a wired or wireless connection. For example, external devices 920 may be connected to the I/O interface via a Bluetooth wireless connection.

In some embodiments, driver status processing system 104 is located in vehicle 204. For example, driver status processing system 104 may include a computer on-board vehicle 204. In some embodiments, driver status processing system 104 includes a mobile device carried by the driver that is located in vehicle 204. For example, driver status processing system 104 may include a laptop computer, a personal digital assistant (PDA), a cellular phone, a tablet computer or the like that is located within vehicle 204. In some embodiments, driver status processing system 104 includes a remote processing device. For example, driver status processing system 104 may include a network server that collects driver status data ("status data") 112 from driver status sensing system 102 via a communications network (e.g., a wireless cellular network), processes status data 112 to determine the driver's status (e.g., health and/or ergonomic status), and provides driver status feedback 114 to driver status feedback system 106 via the communications network. Such an embodiment may off-load processing from a device in the vehicle to a centralized server.

FIG. 10 is a block diagram that illustrates driver monitoring system 100 including components of driver status feedback system 106 in accordance with one or more embodiments of the present invention. In some embodiments, driver status feedback system 109 includes display device 250, audio device 252, a vehicle controller 1002, a driver seat controller 1004, a pedal controller 1006, a steering wheel controller 1008, and/or a rearview mirror controller 1010. In some embodiments, vehicle controller 1002 includes a device that can control various operational aspects of vehicle 104. For example, vehicle controller 1002 may be capable of suspending operation of vehicle (e.g., slowing the vehicle to a stop) in response to receiving a command to do so (e.g., in response to receiving a command to do so via vehicle control feedback 114c, provided by driver status processing system 104). In some embodiments, driver seat controller 1004, pedal controller 1006, steering wheel controller 1008, and rearview mirror controller 1010 each includes a device that can control various operational aspects of driver's seat 210, pedals 214, steering wheel 216, and rearview mirror 218, respectively. For example, driver seat controller 1004 may be capable of adjusting position of driver's seat 210 to a given position (e.g., via controlling positioning motors of driver's seat 210) in response to receiving a command to do so (e.g., in response to receiving a command to do so via driver seat control feedback 114d, provided by driver status processing system 104). Pedal controller 1006 may be capable of adjusting position of pedals 214 to a given position (e.g., via controlling positioning motors of pedals 210) in response to receiving a command to do so (e.g., in response to receiving a command to do so via driver seat control feedback 114e, provided by driver status processing system 104). Steering wheel controller 1008 may be capable of adjusting position of steering wheel 216 to a given position (e.g., via controlling positioning motors of steering wheel 216) in response to receiving a command to do so (e.g., in response to receiving a command to do so via driver seat control feedback 114f, provided by driver status processing system 104). Rearview mirror controller 1010 may be capable of adjusting position of rearview mirror 218 to a given position (e.g., via controlling positioning motors of rearview mirror 218) in response to receiving a command to do so (e.g., in response to receiving a command to do so via driver seat control feedback 114g, provided by driver status processing system 104). Such positioning may be used to adjust driver's seat 210, pedals 214, steering wheel 216, and rearview mirror 218 to correct the driver's body position such that it is ergonomically acceptable.

In some embodiments, driver status processing system 104 collects driver status data ("status data") 112 via driver status sensing system 102, processes status data 112 to determine the driver's status (e.g., health and/or ergonomic status), and provides driver status feedback 114 corresponding to the driver's status to be presented (e.g., displayed or read aloud) to the driver via driver status feedback system 106.

Driver status processing system 104 may use the collected driver status data 112 to assess the driver's health and/or body position. For example, the neural sensor data may be used to determine whether or not the driver is suffering from fatigue or other condition detectable via the driver's brain activity. The seat-bottom sensor data, seat-back sensor data, headrest sensor data, floorboard sensor data, pedal sensor data, steering wheel sensor data, rearview mirror sensor data, and/or position sensor data may be used to determine whether or not the driver's body position in driver's seat 210 is ergonomically correct/acceptable. In some embodiments, the brain/neural sensor data may also be used to assess the driver's body position. For example, the brain/neural sensor data can be used to determine that the driver is uncomfortable in their current body position. In such an embodiment, system 100 may provide for adjusting the driver's body position to increase the driver's comfort level.

Driver status feedback 114 may include content that can be presented to the driver to inform them of their current and/or predicted health and/or ergonomic status. For example, where the collected driver status data 112 indicates that the driver is suffering from fatigue, driver status processing system 104 may generate a health alert to inform the driver of the fatigue condition and suggests that the driver take a break from driving until they have rested for a sufficient period. As a further example, where the collected driver status data 112 indicates that the driver's body position is not ergonomically correct because the driver's seat is too low, driver status processing system 104 may generate an ergonomics alert to inform the driver of the seat being too low condition and provide a suggestion that the driver raise driver's seat 210. Such alerts (e.g., health and/or ergonomic alerts) may be forwarded to driver status feedback system 106 for presentation to the driver. For example, driver status feedback system 106 may read the alert audibly to the driver via speaker 252 located in the vehicle and/or present the alert visually to driver via display device 250 located in the vehicle. Such alerts may help to prevent injury by encouraging the driver to take corrective action prior to the driver actually incurring a physical injury and/or being involved in an accident that may be attributed to the identified issue.

In some embodiments, driver status feedback 114 may provide for implementing an action. For example, where the collected driver status data 112 indicates that the driver is suffering from a critical condition (e.g., has fallen asleep, is suffering a stroke or heart attack, and/or the like), driver status processing system 104 may generate a command to inhibit operation of the vehicle (e.g., slow the vehicle to a stop). As a further example, where the collected driver status data 112 indicates that the driver's body position is not ergonomically correct because the driver's seat is too low, driver status processing system 104 may generate a command raise the driver's seat automatically to a position that corrects the driver's body position such that it is ergonomically acceptable. Such commands may be carried out via the driver status feedback system 106. For example, in response to such commands, vehicle controller 1002 of driver status feedback system 106 may communicate with a control system of the vehicle to bring the vehicle to a stop and/or communicate with a driver seat controller 1004 to automatically adjust the driver's seat 210 to the suggested position. Such actions may help to prevent injury by taking corrective action prior to the driver actually incurring a physical injury and/or being involved in an accident that may be attributed to the identified issue.

FIG. 11 is a flowchart that illustrates a method 1100 of monitoring the status of a driver of a vehicle in accordance with one or more embodiments of the present invention. Method 1100 may include collecting driver status data, as depicted at block 1102. In some embodiments, collecting driver status data includes driver status processing system 104 collecting driver status data 112 from driver status sensing system 102. For example, controller 900 of driver status processing system 104 may collect/receive driver status data 112 via sensors 120 of driver status sensing system 102. Driver status data 112 may include seat sensor data 112a (e.g., including seat-bottom sensor data, seat-back sensor data, and/or headrest sensor data) collected from seat sensors 220 (e.g., seat-bottom sensor 220a,, seat-back sensor 220b,, and/or headrest sensor 220c), floorboard sensor data 112b, collected from floorboard sensors 222, pedal sensor data 112c, (e.g., including gas pedal sensor data, brake pedal sensor data, and/or clutch pedal sensor data) collected from pedal sensors 224 (e.g., gas pedal sensor 224a,, brake pedal sensor 224b, and/or clutch pedal sensor 224c), steering wheel sensor data 112d, (e.g., right steering wheel sensor data and/or left steering wheel sensor data) collected from steering wheel sensors 226 (e.g., right steering wheel sensor 226a, and/or left steering wheel sensor 226b), rearview mirror sensor data 112e, collected from rearview mirror sensors 227, position sensor data 112f, (e.g., shoulder position sensor data, hip position sensor data, knee position sensor data, ankle/foot position sensor data, elbow position sensor data, hand/wrist position sensor data, and/or head position sensor data) collected from position sensors 228 (e.g., shoulder position sensors 228a,, hip position sensors 228b,, knee position sensors 228c,, ankle/foot position sensors 228d,, elbow position sensors 228e,, hand/wrist position sensors 228f,, and/or head position sensors 228g), brain/neural sensor data 112g, collected from brain sensors 229 (e.g., neural sensors 229a) and/or heart rate data 112h, collected from heart rate sensor 219. In some embodiments, driver status data 112 is stored/buffer for processing. For example, controller 900 of driver status processing system 104 may store/buffer the received/collected driver status data 112 in memory 901. In some embodiments, driver status data 112 may be logged for a given period. For example, controller 900 of driver status processing system 104 may log historical driver status data 112 for a preceding time period (e.g., the preceding second, ten seconds, thirty seconds, one-minute, ten-minutes, thirty-minutes, one-hour, twelve hours, twenty four hours, etc.) in memory 901. Such logged data may be used to assess characteristics that are dependent on historical data. For example, a log of brain activity over a given period may be used to track patterns in the driver's brain activity that are indicative of fatigue and/or develop baselines that can be used to identify abnormalities in brain activity that are indicative of a stroke or heart attack.

In some embodiments, collecting driver status data includes collecting driver status data based on schedule. For example, where a driver status collection schedule requires that driver status data 112 be acquired at a given time (e.g., ten seconds after the vehicle is started), controller 900 of driver status processing system 104 may collect/receive driver status data 112 (e.g., a single set of measurements) collected via sensors 120 of driver status sensing system 102 at the given time. Where a driver status collection schedule requires that driver status data 112 be acquired at a regular interval (e.g., once per minute), controller 900 of driver status processing system 104 may collect/receive driver status data 112 (e.g., a single set of measurements) collected via sensors 120 of driver status sensing system 102 at each of the intervals. Where a driver status collection schedule requires that driver status data 112 be acquired continuously (e.g., as fast as can reasonably be acquired by driver status sensing system 102 and/or driver status processing system 104) or substantially continuously (e.g., once per second), controller 900 of driver status processing system 104 may collect/receive driver status data 112 (e.g., a single set of measurements) collected via sensors 120 of driver status sensing system 102 continuously or at least substantially continuously. Such rapid collection of driver status data 112 may enable system 100 to provide the driver with real-time feedback regarding their health and/or ergonomic status when they are driving the vehicle.

In some embodiments, collecting driver status data includes collecting driver status data at a given time and/or during a given period. In some embodiments, a driver status collection schedule may require that driver status data 112 be acquired while the vehicle is being operated (e.g., the ignition is turned on). For example, driver status data 112 may be collected continuously and/or at regular intervals from the time the driver insert the key into the ignition or turns-on the ignition until the driver turns-off the ignition or removes the key from the ignition. In some embodiments, a driver status collection schedule may require that driver status data 112 be acquired during the time when the driver is located in driver's seat 210. For example, driver status data 112 may be continually acquired from seat-bottom sensor 220a, and may be processed (e.g., by controller 900) to determine when the driver is seated in driver's seat 210. When it is determined that the driver is seated in driver's seat 210 (e.g. based on force detected by seat-bottom sensor 220a, that exceeds a threshold force), the collection of driver status data 112 may be triggered such that driver status data 112 is acquired when the driver is located in driver's seat 210. In some embodiments, the collection of driver status data 112 may terminate upon detecting that the driver is no longer seated in the driver's seat. Such embodiments may provide for collection driver status data, processing or driver status data and/or feedback of driver status data when the driver is driving the vehicle.

Method 1100 may include processing the driver status data collected to determine a driver status, as depicted at block 1104. In some embodiments, processing the driver status data collected to determine a driver status includes processing driver status data 112 to determine a health status of the driver and/or an ergonomic status of the driver. For example, controller 900 of driver status processing system 104 may process the collected health data to determine an emotional state of the driver, to determine health characteristics of the driver, to determine whether or not the driver is experiencing a health issue (e.g., that may require a health alert) and/or to determine whether or not the driver is experiencing a health crisis (e.g., a health issue that may require a an action to relive the driver from control of the vehicle). As a further example, controller 900 of driver status processing system 104 may process the collected ergonomic data to determine a body position of the driver, to determine whether the body position of the driver is ergonomically correct/acceptable, to identify adjustments that can be made to correct the driver's body position and/or to identify actions that can be taken to provide the adjustment identified.

Method 1100 may include providing driver status feedback corresponding to the determined driver status, as depicted at block 1106. In some embodiments, providing driver status feedback corresponding to the determined driver status includes providing content for presentation to the driver and/or causing actions to address/correct the current driver status. For example, where it is determined that the driver is in good health (e.g., the driver is not experiencing a health issue/crisis), controller 900 may transmit, to driver status feedback system 106, feedback data 114 (e.g., 114a, and/or 114b) including health status content indicative of the driver being in good health (e.g., a green health status icon and/or a message stating "You are in good health"). Such content may be displayed to the driver via display 250 and/or read audibly to the driver via speaker 252.

Where it is determined that the driver is experiencing a health issue (e.g., the driver is suffering from fatigue), controller 900 may transmit, to driver status feedback system 106, feedback data 114 (e.g., 114a, and/or 114b) including health alert content indicative of the health issue (e.g., a flashing/blinking red health status icon and/or a message stating "You are fatigued. When possible, please stop operating the vehicle and do not drive until you have rested adequately"). Such content may be displayed to the driver via display 250 and/or read audibly to the driver via speaker 252. Such alerts may help to prevent injury by encouraging the driver to take corrective action prior to the driver actually incurring a physical injury and/or being involved in an accident that may be attributed to the identified issue.

Where it is determined that the driver is experiencing a health crisis (e.g., the driver is experiencing a stroke), controller 900 may transmit, to driver status feedback system 106, feedback data 114 (e.g., 114c) including a command to bring the vehicle to a stop, and/or controller 900 may transmit, to driver status feedback system 106, feedback data 114 (e.g., 114a and/or 114b) including a health alert indicative of the health crisis (e.g., a flashing/blinking red health status icon and/or a message stating "You are experiencing a stroke. Please reduce your speed immediately and stop operating the vehicle"). Such content may be displayed to the driver via display 250 and/or read audibly to the driver via speaker 252. In response to the command to bring the vehicle to a stop, vehicle controller 1002 may be employed to reduce the speed of the vehicle and/or slow the vehicle to a stop. Such action may help to reduce the likelihood of accidents that may otherwise occur when the driver that is experiencing a health crisis that renders them unable to adequately control vehicle 204.

Where it is determined that the driver has good ergonomic positioning (e.g., the driver has good body position), controller 900 may transmit, to driver status feedback system 106, feedback data 114 (e.g., 114a, and/or 114b) including ergonomic status content indicative of the driver having good body position (e.g., a green ergonomic status icon and/or a message stating "Your body position is good"). Such content may be displayed to the driver via display 250 and/or read audibly to the driver via speaker 252.

Where it is determined that the driver has poor ergonomic positioning (e.g., the driver has poor body position that is not ergonomically correct/acceptable), controller 900 may transmit, to driver status feedback system 106, feedback data 114 (e.g., 114a, and/or 114b) including content including an ergonomic alert indicative of the need for the driver to adjust body position (e.g., a flashing/blinking red ergonomic status icon and/or a message stating "Your body position is poor. Please move the driver's seat upward"). Such content may be displayed to the driver via display 250 and/or read audibly to the driver via speaker 252. In some embodiments, controller 900 may also transmit feedback data 114 (e.g., 114*d,*, 114*e,*, 114*f,*, and/or 114*g*) including commands to automatically move the driver's seat (e.g., upward) the pedals, the steering wheel and/or the rearview mirror to correct the driver's body position. In response to a command to move the driver's seat upward, for example, driver seat controller 1004 may be employed to actuate motors or similar devices of driver's seat 210 to adjust driver's seat 210 to a position such that the driver's body position is ergonomically correct. Such action may enable automatic adjustment of driver's seat 210 and/or portions of driver's environment 200 with little to no interaction by the driver.

Figure 12:
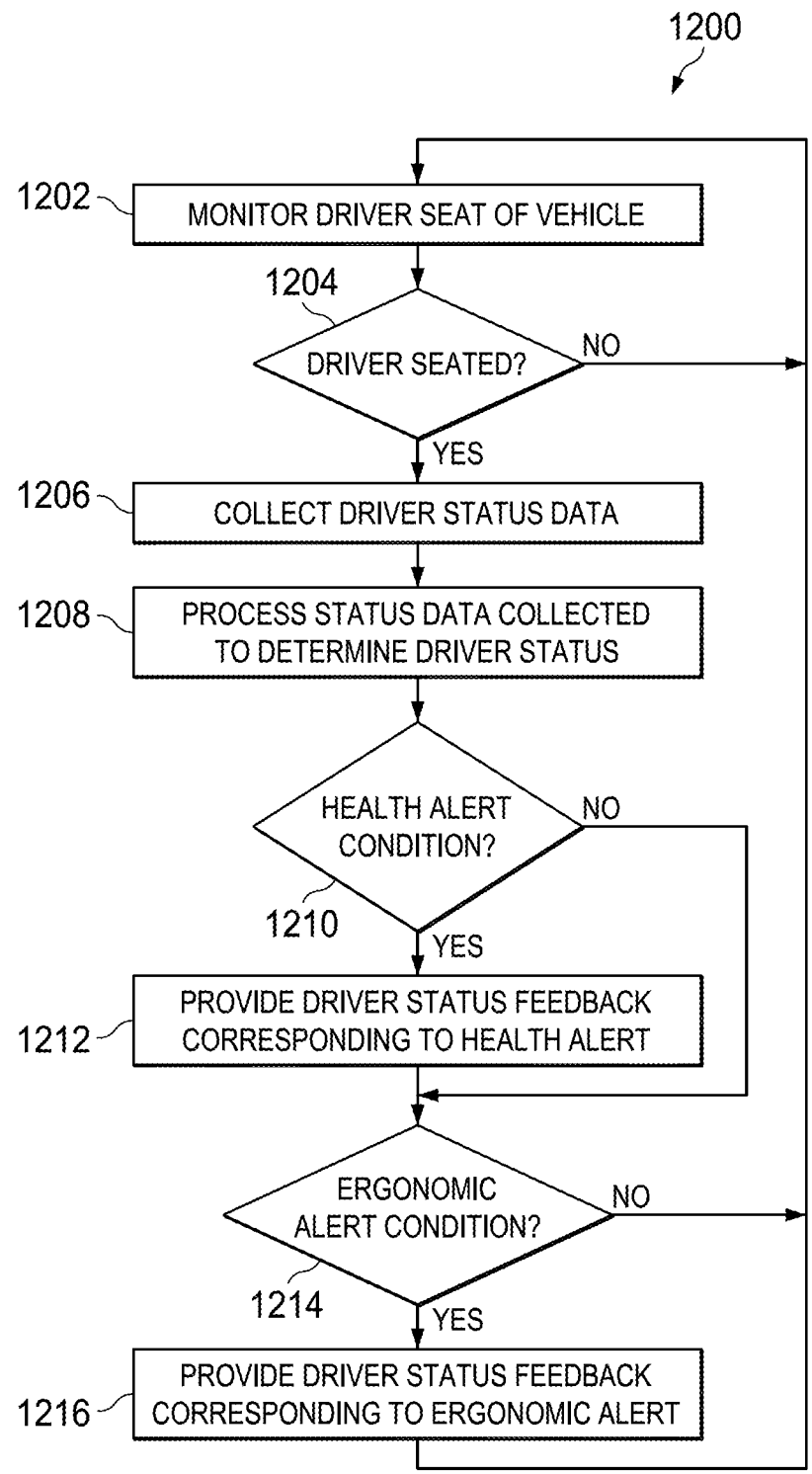
FIG. 12 is a flowchart that illustrates a method of method of monitoring the status of a driver and providing corresponding alerts in accordance with one or more embodiments of the present invention.

FIG. 12 is a flowchart that illustrates a method of method 1200 of monitoring the status of a driver and providing corresponding alerts in accordance with one or more embodiments of the present invention. As discussed herein, method 1200 may provide for monitoring of the driver status while he/she is seated in the driver's seat of a vehicle and may provide feedback (e.g., in the form of information and/or actions) in the event an alert condition (e.g., a health alert or an ergonomic alert condition) is identified.

Method 1200 may include monitoring a driver's seat of a vehicle, as depicted at block 1202. Monitoring a driver's seat of a vehicle may include monitoring a driver's seat of a vehicle to determine if a driver is seated therein. In some embodiments, monitoring a driver's seat of a vehicle to determine if a driver is seated therein may include monitoring data collected from one or more driver status sensors 120 of driver status sensing system 102 to determine whether or not a driver is seated in driver's seat 210. For example, controller 900 may continually acquire and process seat-bottom sensor data from seat-bottom sensor 220*a,* to determine whether a driver is seated in driver's seat 210. In some embodiments, it is determined that a person is seated in driver's seat 210 when the force sensed by seat-bottom sensor 220*a*, exceeds a force threshold. For example, controller 900 may determine that driver 110 is seated in driver's seat 210 upon seat-bottom sensor data being indicative of a force that exceeds 22, kg (50, lbs). It will be appreciated by those skilled in the art that a similar determination may be made based on forces sensed by any of sensors 120 of system 100.

As a further example, controller 900 may continually acquire and process rearview mirror data from rearview mirror sensor 227 to determine whether a driver is seated in driver's seat 210. In some embodiments, it is determined that a person (e.g., driver 110) is seated in driver's seat 210 when image data acquired by rearview mirror sensor indicates that a person is located in driver's seat 210. For example, controller 900 may determine that driver 110 is seated in driver's seat 210 upon rearview mirror sensor data including an image indicative of a person being located in driver seat 210.

Where it is determined that a driver is not seated in the driver seat of the vehicle, method 1200 may include continuing to monitor the driver seat of the vehicle, as depicted at block 1204. Where it is determined that a driver is seated in the driver seat of the vehicle, method 1200 may include proceed to collecting driver status data, as depicted at block 1206.

Collecting driver status data may be the, same or similar to that described with regard to block 1102 of method 1100 (see FIG. 11). For example, controller 900 of driver status processing system 104 may collect/receive/store/log driver status data 112 collected via sensors 120 of driver status sensing system 102. Driver status data 112 may include seat sensor data 112*a* (e.g., including seat-bottom sensor data, seat-back sensor data, and/or headrest sensor data) collected from seat sensors 220 (e.g., seat-bottom sensor 220*a,*, seat-back sensor 220*b,*, and/or headrest sensor 220*c*), floorboard sensor data 112*b*, collected from floorboard sensors 222, pedal sensor data 112*c*, (e.g., including gas pedal sensor data, brake pedal sensor data, and/or clutch pedal sensor data) collected from pedal sensors 224 (e.g., gas pedal sensor 224*a,*, brake pedal sensor 224*b*, and/or clutch pedal sensor 224*c*), steering wheel sensor data 112*d*, (e.g., right steering wheel sensor data and/or left steering wheel sensor data) collected from steering wheel sensors 226 (e.g., right steering wheel sensor 226*a*, and/or left steering wheel sensor 226*b*), rearview mirror sensor data 112*e*, collected from rearview mirror sensors 227, position sensor data 112*f,* (e.g., shoulder position sensor data, hip position sensor data, knee position sensor data, ankle/foot position sensor data, elbow position sensor data, hand/wrist position sensor data, and/or head position sensor data) collected from position sensors 228 (e.g., shoulder position sensors 228*a,*, hip position sensors 228*b,*, knee position sensors 228*c,*, ankle/foot position sensors 228*d,*, elbow position sensors 228*e,*, hand/wrist position sensors 228*f,*, and/or head position sensors 228*g*), brain/neural sensor data 112*g*, collected from brain sensors 229 (e.g., neural sensors 229*a*) and/or heart rate data 112*h*, collected from heart rate sensor 219.

Method 1200 may include processing the driver status data collected to determine a driver status, as depicted at block 1202. Processing the status data collected to determine a driver status may be the same or similar to that described above with regard to block 1104 of method 1100 (see FIG. 11). In some embodiments, processing the driver status data collected to assess a driver status includes processing driver status data 112 to determine a health status of the driver and/or an ergonomic status of the driver. For example, controller 900 of driver status processing system 104 may process the collected health data to determine a health status including an emotional state, health characteristics/conditions, health issues, health crises, and/or the like for the driver. As a further example, controller 900 of driver status processing system 104 may process the collected ergonomic data to determine an ergonomic status including a body position of the driver, differences between an ergonomically correct body position and the driver's current body position, adjustments that can be made to correct the driver's body position and/or adjustment in the driver's environment that can be made to provide for the identified adjustments in body position.

In some embodiments, an emotional state for the driver is determined based at least in part on brain/neural data 112*g*, received from brain sensors 229. For example, controller 900 of driver status processing system 104 may process neuro-signals (e.g., including alpha, beta, gamma, and delta waves) of brain/neural data 112*g*, to determine the driver's current emotional state, including, for example, whether the driver is happy, sad, excited, angry, distracted, etc.). In some embodiments, the emotional state is determined based on other forms of brain activity. For example, controller 900 of driver status processing system 104 may process neuro-signals to determine the driver's thoughts (e.g., cognitive thoughts, subconscious thoughts, intent, etc.) and the thoughts may be used to determine that the driver is distracted (e.g., thinking about things other than driving), angry (e.g., having negative thoughts other driver's), and/or the like.

In some embodiments, health conditions for the driver are determined based on driver status data 112 received from one or more of sensors 120. For example, controller 900 of driver status processing system 104 may process driver status data 112 to determine whether the driver is distracted, fatigued, has fallen asleep, is suffering a stroke/heart-attack, and/or the like. In some embodiments, a determination of whether the driver is fatigued is based on the driver's brain activity. For example, controller 900 may determine that the driver is suffering from fatigue based on brain/neural data 112g, indicative of an abnormally low amount of brain activity. In some embodiments, the driver's fatigue is based on the driver's eye movement. For example, controller 900 may determine that the driver is suffering from fatigue based on rearview mirror data 112e, including images that indicative of an abnormally low amount of eye movement (e.g., the driver is focusing on one location which is indicative of the driver experiencing tunnel vision).

In some embodiments, a determination of whether the driver has fallen asleep is based on the driver's brain activity. For example, controller 900 may determine that the driver is asleep based on brain/neural data 112g, indicative of a sleep state. In some embodiments, the driver's fatigue is based on the driver's eye position. For example, controller 900 may determine that the driver is suffering from fatigue based on rearview mirror data 112e, including images that indicative of the driver's eye being closed for at least a threshold period of time (e.g., greater than three seconds).

In some embodiments, a determination of whether the driver is suffering a stroke is based on the driver's brain activity. For example, controller 900 may determine that the driver is suffering a stroke based on brain/neural data 112g, indicative of a rapid loss of brain function in a manner that is consistent with a stroke caused by a disturbance in blood flow to the brain In some embodiments, a determination of whether the driver is suffering a heart-attack is based on the driver's heart rate. For example, controller 900 may determine that the driver is suffering a heart attack based on heart rate data 112 indicative of the driver's heart rate fluctuating abnormally in a manner consistent with a heart attack.

In some embodiments, the ergonomic status for the driver is determined based on driver status data 112 received from one or more of sensors 120. For example, controller 900 of driver status processing system 104 may process driver status data 112 to determine whether the driver is situated in an ergonomically correct/acceptable body position.

Figure 13:
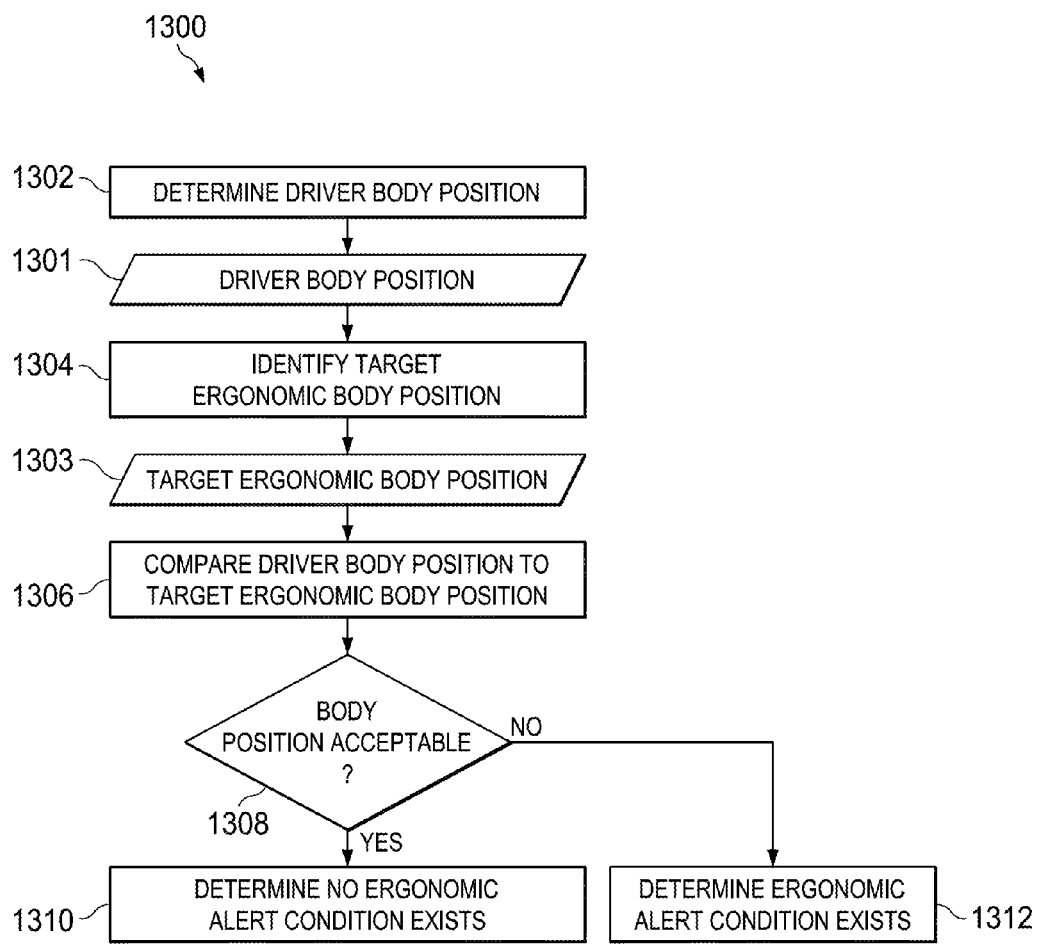
FIG. 13 is a flowchart that illustrates a method for determining an ergonomic status for the driver in accordance with one or more embodiments of the present invention.

FIG. 13 is a flowchart that illustrates a method 1300 for determining an ergonomic status for the driver in accordance with one or more embodiments of the present invention. Method 1300 may include determining a driver body position 1301, as depicted at block 1302. In some embodiments, determining a driver body position includes determining the current body position of the driver based on current driver status data 112. For example, controller 900 of driver status processing system 104 may process driver status data 112 to determine the driver's current body position. In some embodiments, the driver's current body position is based on seat sensor data 112a, (e.g., including seat-bottom sensor data, seat-back sensor data, and/or headrest sensor data), floorboard sensor data 112b,, pedal sensor data 112c, (e.g., including gas pedal sensor data, brake pedal sensor data, and/or clutch pedal sensor data), steering wheel sensor data 112d, (e.g., right steering wheel sensor data and/or left steering wheel sensor data), rearview mirror sensor data 112e, collected from rearview mirror sensors 227, position sensor data 112f (e.g., shoulder position sensor data, hip position sensor data, knee position sensor data, ankle/foot position sensor data, elbow position sensor data, hand/wrist position sensor data, and/or head position sensor data), and/or brain/neural sensor data 112g, collected from brain sensors 229.

In some embodiments, seat sensor data 112a, is used to assess how the driver's buttocks/upper-legs, back and head are supported by corresponding portions of driver's seat 210a. For example, controller 900 of driver status processing system 104 may process seat-bottom sensor data, seat-back data and/or headrest sensor data to determine a supporting force, if any, exerted by upper-seat surface 230a,, back-seat surface 232a,, and/or headrest-support surface 234a,, respectively.

In some embodiments, floorboard sensor data 112b, is used to assess how the driver's feet are supported by floorboard 212. For example, controller 900 of driver status processing system 104 may process floorboard sensor data 112b, to determine a supporting force, if any, exerted by floorboard surface 212.

In some embodiments, pedal sensor data 112c, is used to assess whether the driver's feet reach pedals 214. For example, controller 900 of driver status processing system 104 may process gas-pedal sensor data, break-pedal sensor data and/or clutch pedal sensor data to determine a contact force, if any, exerted by the driver's feet on gas pedal 214a,, brake pedal 214b,, and/or clutch pedal 214c,, respectively.

In some embodiments, steering wheel sensor data 112d, is used to assess where the driver's hands are located on steering wheel 216. For example, controller 900 of driver status processing system 104 may process right steering wheel sensor data and/or left steering wheel sensor data to determine a contact force, if any, exerted by the driver's hands at the location of right steering wheel sensor 226a, and/or left steering wheel sensor 226b,, respectively.

In some embodiments, rearview mirror sensor data 112e, is used to assess various aspects of the driver's body position. For example, controller 900 of driver status processing system 104 may process rearview sensor data 112e, (e.g., including 2D or 3D still or video images of the driver) to determine the driver's eye position relative to the rear view mirror, shoulder position, hip/waist position, leg position (e.g., including knee position and ankle/foot position), arm position (e.g., including elbow position and hand/wrist position), and/or head position.

In some embodiments, position sensor data 112f, is used to assess various aspects of the driver's body position. For example, controller 900 of driver status processing system 104 may process position sensor data 112f, (e.g., 3D coordinates) to determine the driver's shoulder position, hip/waist position, leg position (e.g., including knee position and ankle/foot position), arm position (e.g., including elbow position and hand/wrist position), and/or head position.

In some embodiments, brain/neural sensor data 112g, is used to assess the driver's comfort level with their body position. For example, controller 900 of driver status processing system 104 may process brain/neural sensor data 112g, to determine the driver's level of discomfort based on the sensed brain/neural activity.

Method 1300 may include identifying a target ergonomic body position 1303, as depicted at block 1304. A target ergonomic body position may include a desired body position for driver while seated in a driver's seat of a vehicle. Target ergonomic body position 1303 may define desired characteristics for a driver's eye position, contact with the bottom back and headrest of the driver's seat, weight distribution within the driver's seat, foot contact with the floorboard, foot contact with pedals, the driver's shoulder position, hip/waist position, leg position (e.g., including knee position and ankle/foot position), arm position (e.g., including elbow position and hand/wrist position), head position and/or the like. Target ergonomic body position 1303 may define acceptable ranges for body position characteristics.

Figure 14:
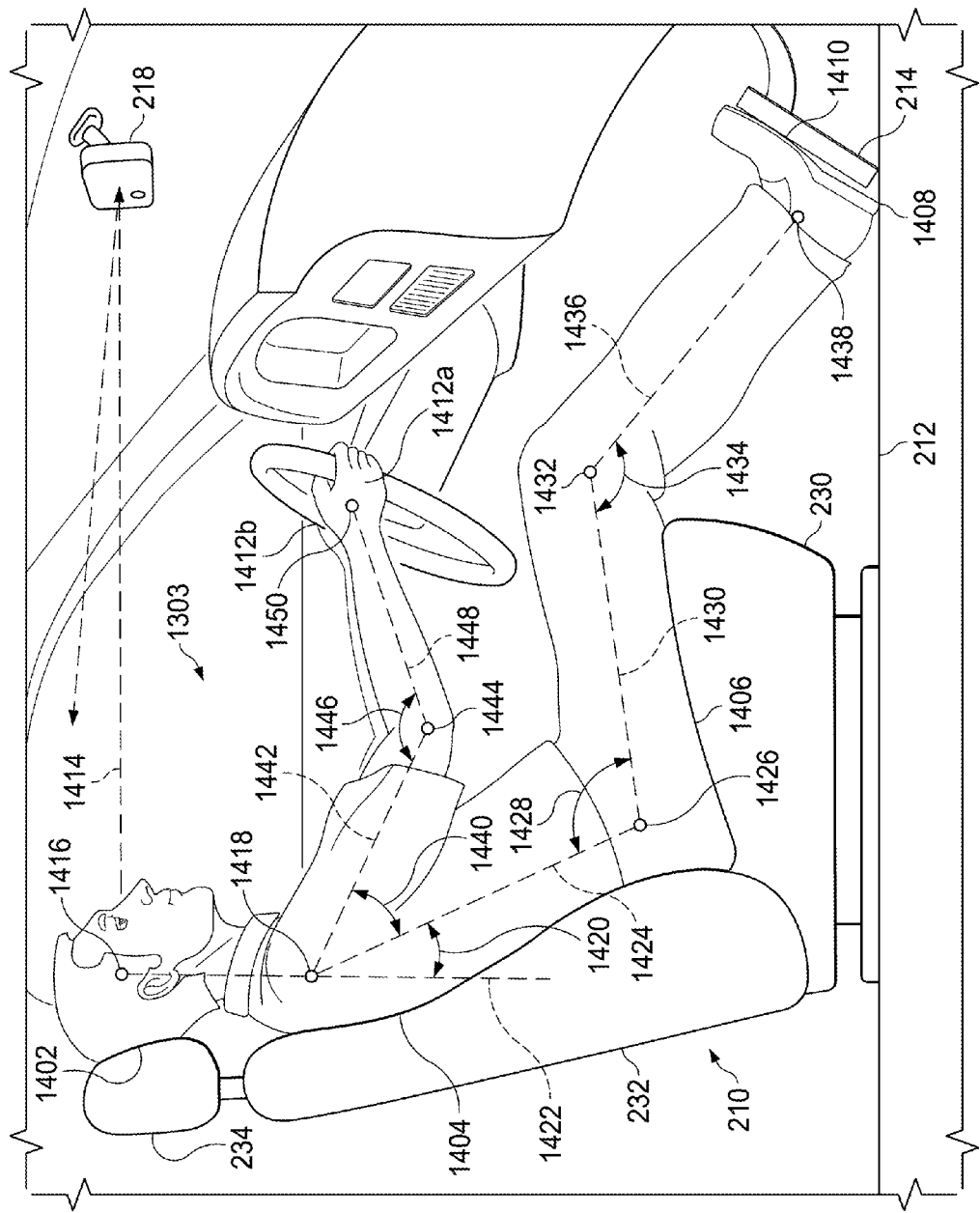
FIG. 14 illustrates characteristics of a target ergonomic body position for a driver in accordance with one or more embodiments of the present invention.

FIG. 14 is illustrates characteristics of a target ergonomic body position for a driver ("ergonomic body position") 1303 in accordance with one or more embodiments of the present invention. Target ergonomic body position 1303 may include some or all of the following ergonomic body position characteristics: the back of the driver's head contacting headrest 234 (see headrest contact point 1402); the driver's back contacting seat-back 232 (see seat-back contact point 1404); the driver's buttock/upper legs contacting seat-bottom 230 (see leg contact point 1406); the driver's feet are contacting floorboard 212 (see floorboard contact point 1408); the driver's feet contacting at least one of pedals 214 (see pedal contact point 1410); the driver's hands contacting steering wheel 214 at the "2, o'clock" and "10, o'clock" positions (see steering wheel contact points 1412a, and 1412b); the driver's eye level and rearview mirror angle being such that the driver does not have to raise or lower their head to see rearward of the vehicle using rearview mirror 218 (see eye direction 1414); the driver's head (see head location 1416) located vertically over the driver's shoulder (see shoulder location 1418); the driver's back being angled 30° from vertical (see back angle 1420 between vertical axis 1422 and torso line 1424 extending from shoulder location 1418 to hip location 1426); the angle between the driver's torso and upper leg being 105° (see upper leg angle 1428 between torso line 1424 and upper leg line 1430 extending from hip location 1426 to knee location 1432); the angle between the driver's upper leg and lower leg being 135° (see knee angle 1434 between upper leg line 1430 and lower leg line 1436 extending from knee location 1430 to ankle/foot location 1438); the angle between the driver's torso line 1424 and arm being 45° (see shoulder angle 1440 between torso line 1424 and upper arm line 1442 extending from shoulder location 1418 to elbow location 1444); the angle between the driver's upper arm and lower arm being 140° (see elbow angle 1446 between upper arm line 1442 and lower arm line 1448 extending from elbow location 1444 to wrist/hand location 1450; an 80/20, force distribution ratio between a force of driver's buttock/upper legs supported by seat-bottom 230 (see leg contact point 1406) and the force of driver's back supported by seat-back 232 (see seat-back contact point 1404) (a "seat bottom/back force ratio"); and/or the like.

In some embodiments, ergonomic body position characteristics may include acceptable range for one or more of the characteristics. For example, body position 1303 may include some or all of the following ergonomic body position acceptable ranges for the characteristics: back angle 1420 between 25° and 35°; upper leg angle 1428 between 100° and 110°; knee angle 1434 between 130° and 140°; shoulder angle 1440 between 40° and 50°; elbow angle 1446 between 135° and 145°; seat bottom/back force ratio between 70/30, and 90/10;, and/or the like. In such an embodiment, the driver may be considered to have good/acceptable body position if they meet the ergonomic body position characteristics (e.g., the body position characteristics fall within the acceptable ranges of target ergonomic body position 1303).

In some embodiments, target ergonomic body position 1303 is stored in memory 901. Target ergonomic body position 1303 may include ergonomic body position data including some or all of the ergonomic body position characteristics of target ergonomic body position 1303. In some embodiments, identifying a target ergonomic body position includes identifying one or more characteristics of an ergonomic body position. For example, identifying a target ergonomic body position may include controller 900 retrieving and/or otherwise accessing/referencing the ergonomic body position characteristics/data stored in memory 901.

In some embodiment, determining a driver body position includes determining characteristic of the driver's body position that correspond to characteristics of target ergonomic body position 1303. For example, controller 900 of driver status processing system 104 may process the most recent driver status data 112 received to determine some or all of the following: whether the back of the driver's head is contacting headrest 234; whether the driver's back is contacting seat-back 232; whether the driver's buttock/upper legs are contacting seat-bottom 230; whether the driver's feet are contacting floorboard 212; whether the driver's feet are contacting at least one of pedals 214; whether the driver's hands are contacting steering wheel 214 at the "2, o'clock" and "10, o'clock" positions; whether the driver's eye level and rearview mirror angle is such that the driver does not have to raise or lower their head to see rearward of the vehicle using rearview mirror 218; whether the driver's back angle 1420 is between 25°, and 35°;, whether the driver's upper leg angle 1428 is between 100°, and 110°;, whether the driver's knee angle 1434 is between 130° and 140°; whether the driver's shoulder angle 1440 is between 40° and 50°; whether the driver's elbow angle 1446 between 135° and 145°; whether the driver's seat bottom/back force ratio is between 70/30, and 90/10;, and/or the like.

In some embodiments, controller 900 of driver status processing system 104 may determine that the back of the driver's head is contacting headrest 234 where it is determined that a supporting force of at least a threshold force value (e.g., 1, kg (2, lbs.)) is exerted by headrest-support surface 234a. In some embodiments, controller 900 of driver status processing system 104 may determine that the back of the driver's head is not contacting headrest 234 where it is determined that a supporting force of at least the threshold force value is not exerted by headrest-support surface 234a.

In some embodiments, controller 900 of driver status processing system 104 may determine that the driver's back is contacting seat-back 232 where it is determined that a supporting force of at least a threshold force value (e.g., 10, kg (22, lbs.)) is exerted by back-seat surface 232a. In some embodiments, controller 900 of driver status processing system 104 may determine that the driver's back is not contacting seat-back 232 where it is determined that a supporting force of at least the threshold force value is not exerted by back-seat surface 232a.

In some embodiments, controller 900 of driver status processing system 104 may determine that the driver's buttock/upper legs are contacting seat-bottom 230 where it is determined that a supporting force of at least a threshold force value (e.g., 50, kg (110, lbs.)) is exerted by back-seat surface 232a. In some embodiments, controller 900 of driver status processing system 104 may determine that the driver's buttock/upper legs are not contacting seat-bottom 230 where it is determined that a supporting force of at least the threshold force value is not exerted by back-seat surface 232a.

In some embodiments, controller 900 of driver status processing system 104 may determine that the driver's feet are contacting floorboard 212 where it is determined that a supporting force of at least a threshold force value (e.g., 1, kg (2, lbs.)) is exerted by floorboard surface 212. In some embodiments, controller 900 of driver status processing system 104 may determine that the driver's feet are not contacting floorboard 212 where it is determined that a supporting force of at least the threshold force value is not exerted by floorboard surface 212.

In some embodiments, controller 900 of driver status processing system 104 may determine that the driver's feet are contacting (e.g., reaching) at least one of pedals 214 where it is determined that a force of at least a threshold force value (e.g., 1, kg (2, lbs.)) is exerted on gas pedal 214a,, brake pedal 214b,, and/or clutch pedal 214c. In some embodiments, controller 900 of driver status processing system 104 may determine that the driver's feet are not contacting at least one of pedals 214 where it is determined that a force of at least the threshold force value is not exerted on gas pedal 214a,, brake pedal 214b,, and/or clutch pedal 214c.

In some embodiments, controller 900 of driver status processing system 104 may determine that the driver's hands are contacting steering wheel 214 at the "2, o'clock" and "10 o'clock" positions where it is determined that a force of at least a threshold force value (e.g., 0.5, kg (1, lbs.)) is exerted at the location of right steering wheel sensor 226a, and left steering wheel sensor 226b. In some embodiments, controller 900 of driver status processing system 104 may determine that the driver's hands are not contacting steering wheel 214 at the "2, o'clock" and "10, o'clock" positions where it is determined that a force of at least a threshold force value is not exerted at the location of right steering wheel sensor 226a, or left steering wheel sensor 226b.

In some embodiments, controller 900 of driver status processing system 104 may determine that the driver's eye level and rearview mirror angle are sufficient such that the driver does not have to raise or lower their head to see rearward of the vehicle using rearview mirror 218 where the driver's eye and the rear of the vehicle are in field of view of the camera. In some embodiments, controller 900 of driver status processing system 104 may determine that the driver's eye level and rearview mirror angle are not sufficient where the driver's eyes or the rear of the vehicle are in the field of view of the camera.

In some embodiments, controller 900 of driver status processing system 104 may determine the positions and angles of the various locations based on position sensor data and/or rearview mirror sensor data. For example, controller 900 may use coordinates for hip position 1426 (e.g., provided by hip position sensor 229b), knee position 1432 (e.g., provided by knee position sensor 229c) and/or foot/ankle position 1438 (e.g., provided by foot/ankle position sensor 229d) to determine knee angle 1434. Other positions and/or angles may be determined in a similar manner.

In some embodiments, controller 900 of driver status processing system 104 may determine that the driver's seat bottom/back force ratio based on seat-bottom sensor data provided by seat-bottom sensor 220a, and seat-back sensor data provided by seat-back sensor 220b. For example, it may be determined that the driver's seat bottom/back force ratio is 80/20 where seat-bottom sensor force data is indicative of a force of 80, kg (176, lbs.) and seat-back sensor data is indicative of a force of 20, kg (44, lbs.)

Determined body position 1301 may be indicative of some or all of the determined characteristics of body position. In some embodiments, determined body position 1301 is stored in memory 901.

Method 1300 may include comparing the driver body position to the target ergonomic position, as depicted at block 1306. In some embodiments, comparing the driver body position to the target ergonomic position includes comparing characteristics of target ergonomic body position 1303 to the determined characteristics of driver body position 1301 corresponding thereto to identify whether the driver bod position matches the target body position (e.g., exactly matches and/or falls within acceptable ranges for the characteristics). Method 1400 may include determining whether or not body position 1301 is acceptable (e.g., ergonomic), as depicted at block 1308. In some embodiments, determining whether or not body position 1301 is acceptable is based on the comparison of driver body position 1301 to target ergonomic position 1303. In some embodiments, it is determined that body position 1301 is not acceptable (e.g., not ergonomic) where one or more of the characteristics of target ergonomic body position 1303 are not satisfied by the corresponding characteristics of driver body position 1301. For example, it may be determined that body position 1301 is not acceptable where driver body position 1301 indicates that the driver's head is not contacting the headrest, the driver's knee angle 1434 is 125° and/or the like. In some embodiments, it is determined that body position 1301 is acceptable (e.g., ergonomic) where all of the characteristics of driver body position 1301 satisfy corresponding characteristics of target ergonomic body position 1303. For example, it may determined that body position 1301 is acceptable where driver body position 1301 indicates that the back of the driver's head is contacting headrest 234; the driver's back is contacting seat-back 232; the driver's buttock/upper legs are contacting seat-bottom 230; the driver's feet are contacting floorboard 212; the driver's feet are contacting at least one of pedals 214; the driver's hands are contacting steering wheel 214 at the "2, o'clock" and "10, o'clock" positions; the driver's eye level and rearview mirror angle is such that the driver does not have to raise or lower their head to see rearward of the vehicle using rearview mirror 218; the driver's back angle 1420 is between 25° and 35°; the driver's upper leg angle 1428 is between 100° and 110°; the driver's knee angle 1434 is between 130° and 140°; the driver's shoulder angle 1440 is between 40° and 50°; the driver's elbow angle 1446 between 135° and 145°; and the driver's seat bottom/back force ratio is between 70/30, and 90/10.

Where it is determined that the driver body position 1301 is acceptable, at block 1308, method 1400 may include proceeding to determining that an ergonomic alert condition does not exists, as depicted at block 1310. Where it is determined that the driver body position 1301 is not acceptable, at block 1308, method 1300 may include proceeding to determining that an ergonomic alert condition does exists, as depicted at block 1312. Thus, in some embodiments, an ergonomic alert condition exists where one or more characteristics/requirements of target ergonomic body position 1303 are not satisfied by body position 1301. In some embodiments (as discussed in more detail below), in response to a determination that an ergonomic alert exists, an ergonomic alert is provided to the driver that includes content indicative of the one or more characteristics of target ergonomic body position 1303 that are not satisfied and/or suggestions to correct body position 1301 and/or feedback to cause actions to correct body position 1301 such that it meets the requirements of target ergonomic body position 1303 and is, thus, acceptable.

As depicted in FIG. 12, method 1200 may include determining whether a health alert condition exists as depicted at block 1210. In some embodiments, it may be determined that the driver is experiencing a health alert condition where it is determined that the driver is experiencing a health condition (e.g., the driver is experiencing fatigue and/or the like) and/or a health crisis (e.g., has fallen asleep, is experiencing a stroke or heart attack, and/or the like). In response to determining that a health alert condition exists, method 1200 may proceed to providing driver status feedback corresponding to the health alert, as depicted at block 1212. In some embodiments, providing driver status feedback corresponding to the health alert may include presenting content to the driver that is indicative of the heath condition and/or crisis that spawned the health alert and/or initiating action to address any issues that may result from the heath condition and/or crisis.

Where, for example, it has been determined that the driver is suffering from fatigue, controller 900 may transmit, to driver status feedback system 106, feedback data 114 (e.g., 114a and/or 114b) including health alert content indicative of the health issue (e.g., a flashing/blinking red health status icon and/or a message stating "You are fatigued. When possible, please stop operating the vehicle and do not drive until you have rested adequately"). Such health alert content may be displayed to the driver via display 250 and/or read audibly to the driver via speaker 252. For example, the flashing/blinking red health status icon and the message stating "You are fatigued. When possible, please stop operating the vehicle and do not drive until you have rested adequately" may be displayed to the driver via display 250 while the message "You are fatigued. When possible, please stop operating the vehicle and do not drive until you have rested adequately" is read aloud via speaker 252. Such alerts may help to prevent injury by encouraging the driver to take corrective action prior to the driver actually incurring a physical injury and/or being involved in an accident that may be attributed to the identified issue.

Figure 15A:
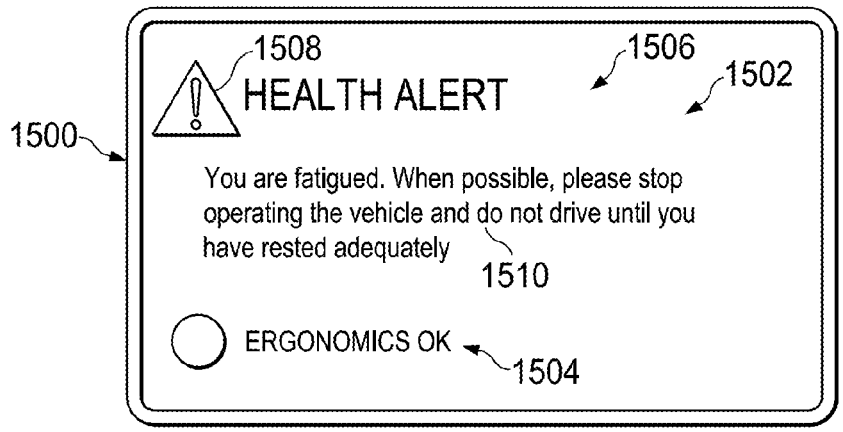
FIGS. 15A-15C illustrate exemplary driver status displays including a health status and an ergonomic status for the driver in accordance with one or more embodiments of the present invention.

FIG. 15A illustrates an exemplary driver status display 1500 including a health status 1502 and an ergonomic status 1504 in accordance with one or more embodiments of the present invention. As depicted, health status 1502 includes a health alert 1506. Health alert 1506 may include may include a flashing/blinking red health status icon 1508 accompanied by health status alert message 1510. Ergonomics status 1504 may be indicative of the current ergonomic status for the driver. For example, where the driver's body position is acceptable, ergonomic status 1504 may include a round (e.g., green) icon accompanied by the message "Ergonomics OK", indicative of the absence of an ergonomic alert condition.

Where, for example, it is determined that the driver is experiencing a health crisis (e.g., the driver is experiencing a stroke), controller 900 may transmit, to driver status feedback system 106, feedback data 114 (e.g., 114c) including a command to bring the vehicle to a stop, and/or controller 900 may transmit, to driver status feedback system 106, feedback data 114 (e.g., 114a, and 114b) including a health alert indicative of the health crisis (e.g., a flashing/blinking red health status icon and/or a message stating "You are experiencing a stroke. Please reduce your speed immediately and stop operating the vehicle"). Such content may be displayed to the driver via display 250 and/or read audibly to the driver via speaker 252. In response to the command to bring the vehicle to a stop, vehicle controller 1002 may be employed to reduce the speed of the vehicle and/or slow the vehicle to a stop. Such action may help to reduce the likelihood of accidents that may otherwise occur when the driver that is experiencing a health crisis and is unable to adequately control vehicle 204. Such alerts and/or actions may help to prevent injury by injury by encouraging the driver to take corrective action and/or taking corrective action prior to the driver actually incurring a physical injury and/or being involved in an accident that may be attributed to the identified issue.

Figure 15B:
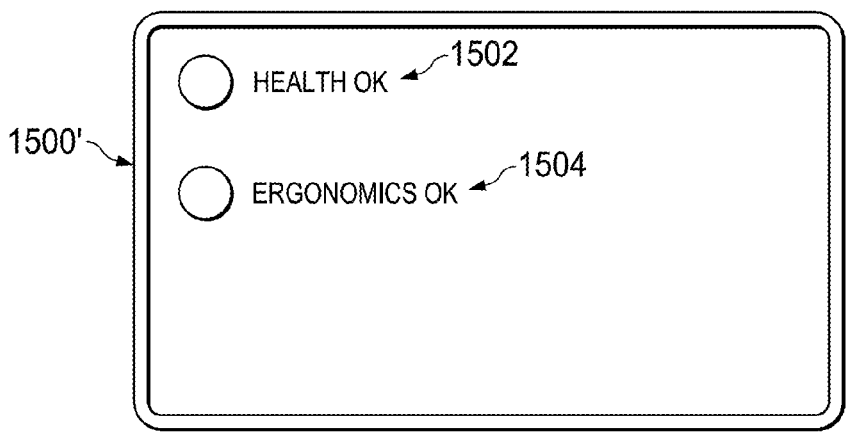

When a health alert condition does not exist, no health alert may be displayed to the user and/or a health status may be displayed indicative of the absence of a health alert condition. FIG. 15B illustrates an exemplary driver status display 1500' including a health status 1502 and an ergonomic status 1504 in accordance with one or more embodiments of the present invention. As depicted, health status 1502 includes a round (e.g., green) icon accompanied by the message "Helath OK", indicative of the absence of a health alert condition.

As depicted in FIG. 12, method 1200 may include determining whether an ergonomic alert condition exists as depicted at block 1214. In some embodiments, it may be determined that an ergonomic alert condition does or does not exists in accordance with the techniques described at blocks 1308, 1310 and 1312 of method 1300 (see FIG. 13). For example, it may be determined that an ergonomic alert condition exists where one or more characteristics/requirements of target ergonomic body position 1303 are not satisfied by corresponding characteristics of body position 1301, and it may be determined that an ergonomic alert condition does not exist where all of the characteristics/requirements of target ergonomic body position 1303 are satisfied by corresponding characteristics of body position 1301. In response to determining that an ergonomic alert condition does exists, method 1200 may proceed to providing driver status feedback corresponding to the ergonomic alert, as depicted at block 1216. In some embodiments, providing driver status feedback corresponding to the ergonomic alert may include presenting content to the driver that is indicative of the ergonomic condition(s) that spawned the ergonomic alert, providing suggestions to correct the ergonomic condition(s) that spawned the ergonomic alert and/or initiating action to address any issues that may result from the heath condition and/or crisis. Such alerts may help to prevent injury by encouraging the driver to take corrective action prior to the driver actually incurring a physical injury and/or being involved in an accident that may be attributed to the identified issue.

Where, for example, it is determined that the driver has unacceptable body position, controller 900 may transmit, to driver status feedback system 106, feedback data 114 (e.g., 114a and 114b) including an ergonomic alert indicative of the unacceptable body position and/or suggestions for adjusting the driver's body position such that it is acceptable (e.g., a flashing/blinking red ergonomic status icon and/or a message stating "Your body position is incorrect. Please move the driver's seat upward"). Such ergonomic alert content may be displayed to the driver via display 250 and/or read audibly to the driver via speaker 252. For example, the flashing/blinking red ergonomic status icon and the message stating "Your body position is incorrect. Please move the driver's seat upward" may be displayed to the driver via display 250 while the message "Your body position is incorrect. Please move the driver's seat upward" is read aloud via speaker 252.

Figure 15C:
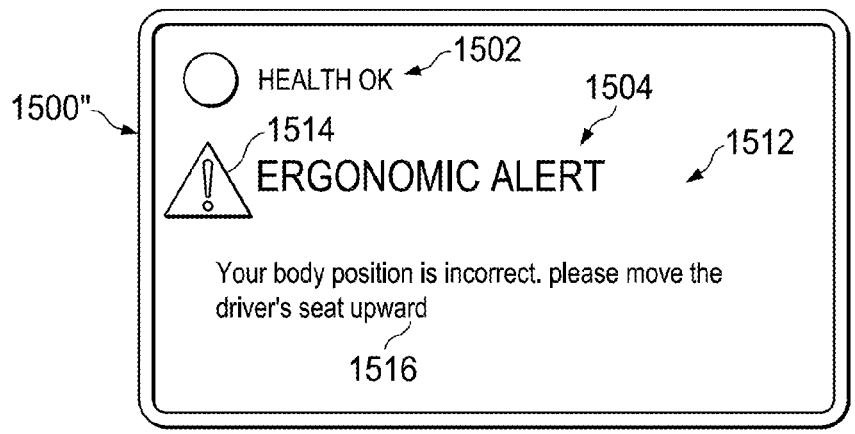

FIG. 15C illustrates an exemplary driver status display 1500" including a health status 1502 and an ergonomic status 1504 in accordance with one or more embodiments of the present invention. As depicted, ergonomic status 1504 includes an ergonomic alert 1512. Ergonomic alert 1512 may include may include a flashing/blinking red ergonomic status icon 1514 accompanied by health status alert message 1516. Health status 1502 may be indicative of the current health status for the driver. For example, where the driver is not experiencing a health alert condition, health status 1502 may include a round (e.g., green) icon accompanied by the message "Health OK", indicative of the absence of a health alert condition.

In some embodiments, providing driver status feedback corresponding to the ergonomic alert includes controller 900 transmitting feedback data 114 (e.g., 114d,, 114e,, 114f, and/or 114g) including commands to automatically move the driver's seat (e.g., upward) the pedals, the steering wheel and/or the rearview mirror to positions that are expected to correct the driver's body position such that the driver's body position is ergonomically acceptable body position. In response to a command to move the driver's seat upward, for example, driver seat controller 1004 may be employed to actuate motors or similar devices of driver's seat 210 to adjust driver's seat 210 to a position such that the driver's body position is ergonomically correct. Such action may enable automatic adjustment of driver's seat 210 with little to no interaction by the driver. Such actions may help to prevent injury by taking corrective action prior to the driver actually incurring a physical injury and/or being involved in an accident that may be attributed to the identified issue.

Although certain exemplary embodiments are described with regard to an ergonomic alert relating to a seat height, other embodiments may include similar alerts and feedback relating to any variety of ergonomic conditions. For example, where the driver's knee angle 1434 is less than 130°, similar alerts/command may be provided regarding tilting driver's seat back 210 (e.g., rotating driver seat-bottom 230 counter-clockwise), sliding driver's seat 210 forward to (e.g., toward pedals 214 and/or steering wheel 216) to increase knee angle 1434 to between 130° and 140°, tilting rearview mirror 218 to account for a change in the driver's eye level, retracting steering wheel 216 toward dash to account for the forward movement of driver's seat 210, and/or moving pedals 214 inward to account for the forward movement of driver's seat 210. As another example, where it is determined that the driver's feet are not contacting pedals 214, similar alerts/command may be provided regarding sliding the driver's seat forward to (e.g., toward pedals 214) and/or moving pedals 214 outward (e.g., toward driver's seat 210) to bring the driver's feet into contact with pedals 214.

When an ergonomic alert condition does not exist, no ergonomic alert may be displayed and/or an ergonomic status may be displayed indicative of the absence of an ergonomic alert condition. FIG. 15B illustrates an exemplary driver status display 1500' including a health status 1502 and an ergonomic status 1504 in accordance with one or more embodiments of the present invention. As depicted, ergonomic status 1504 includes a round (e.g., green) icon accompanied by the message "Ergonomics OK" indicative of the absence of an ergonomic alert condition.

It will be appreciated that methods 1100, 1200 and 1300 are exemplary embodiments of methods that may be employed in accordance with techniques described herein. Methods 1100, 1200 and 1300 may be may be modified to facilitate variations of its implementations and uses. Methods 1100, 1200 and 1300 may be implemented in software, hardware, or a combination thereof. Some or all of the methods 1100, 1200 and 1300 may be implemented by one or more of the modules/applications described herein, such as driver status processing module 908. The order of methods 1100, 1200 and 1300 may be changed, and various elements may be added, reordered, combined, omitted, modified, etc.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

As used throughout this application, the word "may" is used in a permissive sense (i.e., meaning having the potential to), rather than the mandatory sense (i.e., meaning must). The words "include", "including", and "includes" mean including, but not limited to. As used throughout this application, the singular forms "a", "an" and "the" include plural referents unless the content clearly indicates otherwise. Thus, for example, reference to "an element" may include a combination of two or more elements. Unless specifically stated otherwise, as apparent from the discussion, it is appreciated that throughout this specification discussions utilizing terms such as "processing", "computing", "calculating", "determining" or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical electronic or magnetic quantities within memories, registers, or other information storage devices, transmission devices, or display devices of the special purpose computer or similar special purpose electronic processing/computing device.

The techniques described herein may include or otherwise be used in conjunction with techniques described in U.S. Provisional Patent Application No. 61/664,414, filed on Jun. 26, 2012, and titled "SYSTEMS, COMPUTER MEDIUM AND COMPUTER-IMPLEMENTED METHODS FOR MONITORING HEALTH AND ERGONOMIC STATUS OF DRIVERS OF VEHICLES", U.S. Provisional Patent Application No. 61/504,638, filed on Jul. 5, 2011, and titled "SYSTEM, COMPUTER PROGRAM PRODUCT AND COMPUTER-IMPLEMENTED METHOD FOR IMPROVING AND MONITORING THE HEALTH AND PRODUCTIVITY OF EMPLOYEES", U.S. Provisional Patent Application No. 61/659,831, filed on Jun. 14, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,790, filed on Jun. 14, 2012, and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. Provisional Patent Application No. 61/659,796, filed on Jun. 14, 2012, and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,800, filed on Jun. 14, 2012, and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,807, filed on Jun. 14, 2012, and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,810, filed on Jun. 14, 2012, and titled "SYSTEMS, COMPUTER MEDIUM AND COMPUTER-IMPLEMENTED METHODS FOR MONITORING AND IMPROVING BIOMETRIC HEALTH OF EMPLOYEES", U.S. Provisional Patent Application No. 61/659,818, filed on Jun. 14, 2012, and titled "SYSTEMS, COMPUTER MEDIUM AND COMPUTER-IMPLEMENTED METHODS FOR MONITORING AND IMPROVING BIOMECHANICAL HEALTH OF EMPLOYEES", U.S. Provisional Patent Application No. 61/659,824, filed on Jun. 14, 2012, and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", U.S. Provisional Patent Application No. 61/664,387, filed on Jun. 26, 2012, and titled "SYSTEMS, COMPUTER MEDIUM AND COMPUTER-IMPLEMENTED METHODS FOR MONITORING HEALTH OF EMPLOYEES USING MOBILE DEVICES", and U.S. Provisional Patent Application No. 61/664,399, filed on Jun. 26, 2012, and titled "SYSTEMS, COMPUTER MEDIUM AND COMPUTER-IMPLEMENTED METHODS FOR PROVIDING HEALTH INFORMATION TO EMPLOYEES VIA AUGMENTED REALITY DISPLAY", the disclosures of which are each hereby incorporated by reference in their entireties.

In this patent, certain U.S. patents, U.S. patent applications, or other materials (e.g., articles) have been incorporated by reference. The text of such U.S. patents, U.S. patent applications, and other materials is, however, only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference in this patent.

What is claimed is:

1. A system for monitoring a status of a driver when driving a vehicle, the system comprising:
   a driver status sensing system comprising a set of one or more driver status sensors configured to be disposed in the vehicle, the one or more driver status sensors comprising:
      a set of one or more driver's seat sensors configured to output seat data indicative of a position of a head, a torso and a leg of the driver relative to a driver's seat of the vehicle;
      a set of one or more floorboard sensors configured to output floorboard data indicative of a position of feet of the driver relative to a floorboard of the vehicle;
      a set of one or more pedal sensors configured to output pedal data indicative of a position of feet of the driver relative to pedals of the vehicle;
      a set of one or more steering wheel sensors configured to output steering wheel data indicative of a position of hands of the driver relative to a steering wheel of the vehicle;
      a set of one or more rearview mirror sensors configured to output rearview mirror data indicative of a position of eyes of the driver relative to a rearview mirror of the vehicle; and
      a set of one or more brain sensors configured to output neural data indicative of a brain activity of the driver, the set of one or more driver status sensors configured to output driver status data corresponding to at least one of the seat data, the floorboard data, the pedal data, the steering wheel data, the rearview mirror data, and the neural data;
   a driver status processing system configured to:
      receive the driver status data output by the set of one or more driver status sensors;
      process the driver status data to determine whether the driver is experiencing a health condition;
      process the driver status data to determine whether the driver is experiencing a health crisis;
      process the driver status data to determine whether a body position of the drive is ergonomically acceptable;
      in response to determining that the driver is experiencing a health condition, generating a health alert indicative of the health condition that is configured to be displayed to the driver via a display of a driver status feedback system;
      in response to determining that the driver is experiencing a health crisis:
         generate a health alert indicative of the health crisis that is configured to be displayed to the driver via a display of the driver status feedback system; and
         generate a command configured to cause inhibiting of operation of the vehicle; and
      in response to determining that a body position of the drive is not ergonomically acceptable:
         identify adjustments in the body position of the driver that need to be made for the driver to be positioned in an ergonomically acceptable body position; and
         generate an ergonomic alert indicative of adjustments in the body position of the driver that need to be made for the driver to be positioned in an ergonomically acceptable body position that is configured to be displayed to the driver via a display of the driver status feedback system; and
   the driver status feedback system comprising the display, the display being configured to display, to the driver, the health alert indicative of the health condition, the health alert indicative of the health crisis and the ergonomic alert indicative of adjustments in the body position of the driver that need to be made for the driver to be positioned in an ergonomically acceptable body position.

2. A system according to claim 1, wherein processing the driver status data to determine whether a body position of the drive is ergonomically acceptable comprises:
   determining a current body position of the driver based at least in part on the driver status data received;
   identifying a target ergonomic body position;
   comparing the current body position of the driver to the target ergonomic body position identified;
   determining, based at least in part on the comparison, that a characteristic of the current body position of the driver does not satisfy a corresponding characteristic of the target ergonomic body position; and
   determining that an adjustment needs to be made in the body position of the driver such that the characteristic of the current body position of the driver does satisfy the corresponding characteristic of the target ergonomic body position,
   wherein identify adjustments in the body position of the driver that need to be made for the driver to be positioned in an ergonomically acceptable body position comprises identifying the adjustment that needs to be made in the body position of the driver such that the characteristic of the current body position of the driver does satisfy the corresponding characteristic of the target ergonomic body position.

3. A system according to claim 2, wherein the characteristic of the current body position comprises contact of a head of the driver with a headrest, contact of a back of the driver with a seat-back, contact of a buttock/upper legs of the driver with a seat-bottom, contact of feet of the driver with a floorboard, contact of feet of the driver with a pedal, contact of hands of the driver with a steering wheel, an eye level of the driver, a back angle of the driver, an upper leg angle of the driver, a knee angle of the driver, a shoulder angle of the driver, an elbow angle of the driver, or a bottom/back force ratio of the driver.

4. A system according to claim 2, wherein the characteristic of the current body position of the driver comprises a head position, a hand position, a back position or a foot position of the current body position of the driver.

5. A system according to claim 1, wherein the driver status processing system is further configured to, in response to determining that a body position of the driver is not ergonomically acceptable, generate a move command configured to cause automatic movement of at least one of a driver's seat, pedals, a steering wheel or a rearview mirror of the vehicle to cause adjustments in the body position of the driver that need to be made for the driver to be positioned in an ergonomically acceptable body position.

6. A system according to claim 1, wherein the driver status processing system is configured to continuously receive the driver status data, process the driver status data to determine whether the driver is experiencing a health condition, whether the driver is experiencing a health crisis and whether a body position of the drive is ergonomically acceptable such that the driver is provided with real-time feedback indicative of whether the driver is experiencing a health condition, whether the driver is experiencing a health crisis, and whether a body position of the drive is ergonomically acceptable.

7. A system according to claim 1, wherein the health condition comprises fatigue, and wherein the health alert indicative of the health condition comprises a suggestion that the driver suspend driving the vehicle.

8. A system according to claim 1, wherein the command configured to cause inhibiting of operation of the vehicle comprises a command configured to slow the vehicle to a stop.

\* \* \* \* \*

UNITED STATES PATENT AND TRADEMARK OFFICE
CERTIFICATE OF CORRECTION

Page 1 of 1

PATENT NO. : 8,872,640 B2
APPLICATION NO. : 13/540374
DATED : October 28, 2014
INVENTOR(S) : Horseman It is certified that error appears in the above-identified patent and that said Letters Patent is hereby corrected as shown below:

In the Claim
Column 36, line 32, Claim 2 "drive is" should read "driver is".

Signed and Sealed this
Third Day of March, 2015

Michelle K. Lee
*Deputy Director of the United States Patent and Trademark Office*